United States Patent
Radhakrishnan et al.

(10) Patent No.: US 11,523,738 B2
(45) Date of Patent: Dec. 13, 2022

(54) DEVICE AND METHOD FOR DETECTION AND CLASSIFICATION OF PATHOGENS

(71) Applicant: ADIUVO DIAGNOSTICS PVT LTD, Nellore (IN)

(72) Inventors: Geethanjali Radhakrishnan, Chennai (IN); John King, Chennai (IN); Meenatchi U, Vanur Taluk (IN); Aayush Gupta, Panipet (IN)

(73) Assignee: ADIUVO DIAGNOSTICS PVT LTD, Nellore (IN)

( * ) Notice: Subject to any disclaimer, the term of this patent is extended or adjusted under 35 U.S.C. 154(b) by 570 days.

(21) Appl. No.: 16/496,390

(22) PCT Filed: Mar. 22, 2018

(86) PCT No.: PCT/IN2018/050161
§ 371 (c)(1),
(2) Date: Sep. 20, 2019

(87) PCT Pub. No.: WO2018/173073
PCT Pub. Date: Sep. 27, 2018

(65) Prior Publication Data
US 2021/0106231 A1    Apr. 15, 2021

(30) Foreign Application Priority Data
Mar. 22, 2017 (IN) .............................. 201741010111

(51) Int. Cl.
*G01N 21/31* (2006.01)
*G16H 50/20* (2018.01)
(Continued)

(52) U.S. Cl.
CPC ............ *A61B 5/0071* (2013.01); *A61B 5/445* (2013.01); *A61B 5/4842* (2013.01);
(Continued)

(58) Field of Classification Search
CPC ..... A61B 5/0071; A61B 5/445; A61B 5/4842; A61B 5/7246; A61B 5/7267; A61B 5/742;
(Continued)

(56) References Cited

U.S. PATENT DOCUMENTS 6,765,668 B2    7/2004    Gardner et al.
8,417,324 B2    4/2013    Mycek et al.
(Continued)

FOREIGN PATENT DOCUMENTS

WO    WO-03046798 A1 *    6/2003    ......... G01N 30/8655
WO    WO-2007009119 A2 *    1/2007    ......... G01N 15/1463
(Continued)

OTHER PUBLICATIONS

International Application Status Report, dated Sep. 17, 2019, in International Patent Application No. PCT/IN2018/050161.
(Continued)

*Primary Examiner* — David P Porta
*Assistant Examiner* — Fani Polyzos Boosalis
(74) *Attorney, Agent, or Firm* — Knobbe, Martens, Olson & Bear LLP

(57) ABSTRACT

Device and methods for detection and classification of pathogens have an imaging module, an image processing module, and a display module. The imaging module has a plurality of light sources to expose a sample to excitation radiation at various wavelengths. A detector in the imaging module synchronously captures time-resolved fluorescence emission spectra, time-resolved reflectance, and transmittance spectra at multiple spectral bands from the sample. The image processing module resolves the spectra and compares obtained spectral parameters to set of standard parameters provided in a library database to determine a match to detect and classify pathogens.

17 Claims, 17 Drawing Sheets

(51) Int. Cl.
| | |
|---|---|
| A61B 5/00 | (2006.01) |
| G16H 30/40 | (2018.01) |
| G01N 21/64 | (2006.01) |
| G06K 9/62 | (2022.01) |
| G06V 10/60 | (2022.01) |

(52) U.S. Cl.
CPC .......... *A61B 5/7246* (2013.01); *A61B 5/7267* (2013.01); *A61B 5/742* (2013.01); *G01N 21/31* (2013.01); *G01N 21/6408* (2013.01); *G01N 21/6456* (2013.01); *G06K 9/627* (2013.01); *G06V 10/60* (2022.01); *G16H 30/40* (2018.01); *G16H 50/20* (2018.01); *A61B 2576/00* (2013.01); *G01N 2021/6419* (2013.01); *G01N 2201/0221* (2013.01); *G06V 2201/03* (2022.01)

(58) Field of Classification Search
CPC .... A61B 2576/00; G16H 50/20; G16H 30/40; G06V 10/60; G06V 2201/03; G01N 21/31; G01N 21/6408; G01N 21/6456; G01N 2021/6419; G01N 2201/0221; G06K 9/627
See application file for complete search history.

(56) References Cited

U.S. PATENT DOCUMENTS

| | | |
|---|---|---|
| 9,365,883 B2 | 6/2016 | Gannot et al. |
| 10,253,346 B2 | 4/2019 | Auner et al. |
| 10,288,567 B2 | 5/2019 | Butte et al. |
| 2009/0066934 A1 | 3/2009 | Gao et al. |
| 2010/0056928 A1 | 3/2010 | Zuzak et al. |
| 2011/0117025 A1 | 5/2011 | Dacosta et al. |
| 2014/0377795 A1 | 12/2014 | Gannot et al. |
| 2015/0284763 A1 | 10/2015 | Rehse |
| 2015/0044098 A1 | 12/2015 | Smart et al. |
| 2016/0177366 A1 | 1/2016 | Auner et al. |
| 2016/0377547 A1 | 12/2016 | Butte et al. |

FOREIGN PATENT DOCUMENTS

| | | | |
|---|---|---|---|
| WO | WO 2009/140757 A1 | 11/2009 | |
| WO | WO2009140757 A1 | 11/2009 | |
| WO | WO 2014/040168 A1 | 3/2014 | |
| WO | WO 2016/069788 A1 | 5/2016 | |
| WO | WO 2020/148726 A1 | 7/2020 | |

OTHER PUBLICATIONS

International Search Report & Written Opinion, dated Jun. 19, 2018, in International Patent Application No. PCT/IN2018/050161.
Awad, F., Ramprasath, C., Mathivanan, N., Aruna, P.R. & Ganesan, S. Steady-state and fluorescence lifetime spectroscopy for identification and classification of bacterial pathogens. Biomedical Spectroscopy and Imaging, (2014) 3, 381-391.
Rehse, S.J., Mohaidat, Q.I. & Palchaudhuri, S. Towards the clinical application of laser-induced breakdown spectroscopy for rapid pathogen diagnosis: the effect of mixed cultures and sample dilution on bacterial identification. Optical Society of America, (2010) 49(13), C27-35.
Marcu, L. Fluorescence Lifetime Techniques in Medical Applications. Ann Biomed Eng, (2012) 40(2), 304-33.
DaCosta et al., Molecular Fluorescence Excitation-Emission Matrices Relevant to Tissue Spectroscopy, Photochemistry and Photobiology (2003) 78(4) 384-392. Photochem & Photobio, 78(4), 384-392.
Yankelevich, D.R., Ma, D., Liu, J., Sun, Y., Sun, Y., Bec, J., et al. Design and evaluation of a device for fast multispectral time-resolved fluorescence spectroscopy and imaging, Rev Sci Instrum, (2014) 85(3).
Bhatta, H., Goldys, E.M., Learmonth, R. Rapid identification of microorganisms by intrinsic fluorescence. Proceedings of SPIE—The International Society for Optical Engineering, (2005) 5699.
Dartnell, L.R., Roberts, T.A., Moore, G., Ward, J.M., Muller, J. Fluorescence Characterization of Clinically-Important Bacteria. PLoS ONE, (2013) 8(9), 1-13.
Giana, H.E, Silveira Jr., L., Zângaro, R.A. & Pacheco, M.T.T. Rapid Identification of Bacterial Species by Fluorescence Spectroscopy and Classification Through Principal Components Analysis. Journal of Fluorescence, (2003) 13(6), 489-493.
Kittle, D.S., Vasefi, F., Patil, C. G., Mamelak, A., Black, K.L. & Butte, P.V. Time-resolved fluorescence spectroscopy instrumentation and validation. Sci Rep, (2016) 6(38190).
Leblanc, L. & Dufour, É. Monitoring the identity of bacteria using their intrinsic fluorescence. FEMS Microbiology Letters, (2002) 211(2), 147-153.
Awad, F et al., "Steady-state and fluorescence lifetime spectroscopy for identification and classification of bacterial pathogens," Biomedical Spectroscopy and Imaging 3, Jan. 2014, vol. 3, No. 4, pp. 381-391.
Bhatta, "Rapid Identification of Microorganisms by Intrinsic Fluorescence," 2005, Imaging, Manipulation, and Analysis of Biomolecules and Cells: Fundamentals And Applications III, Proc of SPIE, vol. 5699, pp. 9-18.
Bhattacharjee et al., "Metabolic fingerprinting of bacteria by fluorescence lifetime imaging microscopy," 2017, Scientific Reports, 7:3473, pp. 1-10.
Berezin et al., "Fluorescence Lifetime Measurements and Biological Imaging," Chem Rev., May 12, 2010, 110(5), pp. 2641-2684.
Dacosta et al., "Molecular Fluorescence Excitation-Emission Matrices Relevant to Tissue Spectroscopy," Oct. 2003, Photochemistry and Photobiology 2003, vol. 78, Issue 4, pp. 384-392.
Dartnell et al., Fluorescence Characterization of Clinically-Important Bacteria, 2013, PLOS One 8(9): e75270.
Datta et al. "Fluorescence lifetime imaging microscopy: fundamentals and advances in instrumentation, analysis, and applications," Jul. 2020, SPIE, J. Biomed. Opt. vol. 25(7), 071203-1-071203-43.
Eberl et al., "*Pseudomonas aeruginosa* and *Burkholderia cepacia* in cystic fibrosis: genome evolution, interactions and adaptation," Sep. 24, 2004, International Journal of Medical Microbiology, vol. 294, Issues 2-3, pp. 123-131.
Giana et al., "Rapid Identification of Bacterial Species by Fluorescence Spectroscopy and Classification Through Principal Components Analysis," Nov. 2003, Journal of Fluorescence, vol. 13, No. 6, 489-493.
Ingelberts et al., "A proof-of-concept fluorescence lifetime camera based on a novel gated image sensor for fluorescence-guided surgery," Mar. 7, 2019, Proc. SPIE 10862, Molecular-Guided Surgery: Molecules, Devices, and Applications V., 108620C.
Jones et al., In vitro detection of porphyrin-producing wound bacteria with real-time fluorescence imaging, 2020, Future Microbiology, 15(5), 319-332.
Kittle et al., "Real time optical Biopsy: Time-resolved Fluorescence Spectroscopy instrumentation and validation," 2016, Scientific Reports, 6:38190, pp. 1-9.
LeBlanc et al., "Monitoring the identity of bacteria using their intrinsic Fluorescence," Jun. 2002, FEMS Microbiology Leets, vol. 211, Issue 2, pp. 147-153.
Ma et al., (2015). "Technique for real-time tissue characterization based on scanning multispectral fluorescence lifetime spectroscopy (ms-TRFS)," 2015, Biomedical Optics Express, vol. 6(3), pp. 987-1002.
Marcu L., "Fluorescence Lifetime Techniques in Medical Applications," 2012, Ann Biomed Eng, 40(2), 304-331.
MolecuLight i:X® receives FDA 510(k) Clearance for the Device's Ability to Detect Wounds Likely to Contain *Pseudomonas aeruginosa* (PA).
NXP Semiconductors, 1N4148; 1N4448 High-Speed Diodes, Oct. 8, 2004.
Parekh et al., A New Device and Technology for Detecting Bacterial Infection and its Gram Type in Diabetic Foot Ulcer, Jan. 4, 2022, Indian Journal of Surgery.

(56) References Cited

OTHER PUBLICATIONS

Ponikvar, "A simple Subnanosecond Light Pulser," Dec. 2012, IEEE Transactions on nuclear Science, vol. 59, No. 6, pp. 3218-3220.

Price, Nadine, "Routine Fluorescence Imaging to Detect Wound Bacteria Reduces Antibiotic Use and Antimicrobial Dressing Expenditure While Improving Healing Rates: Retrospective Analysis of 229 Foot Ulcers," 2020, Diagnostics, 10, 927, pp. 1-11.

Radhakrishnan, et al., "Rapid handheld screening device to detect skin and soft tissue infections," Proc. SPIE 11211, Photonics in Dermatology and Plastic Surgery 2020, 112110V.

Rehse et al., "Towards the clinical application of laser-induced breakdown spectroscopy for rapid pathogen diagnosis: the effect of mixed cultures and sample dilution on bacterial identification," 2010, Optical Society of America, vol. 49, Issue 13, pp. C27-C35.

Veledar et al., "Simple techniques for generating nanosecond blue light pulses for light emitting diodes," 2007, Measurement Science Technology, vol. 18, No. 1, 131.

Wagniéres et al., "Frequency-Domain Fluorescence Lifetime Imaging for Endoscopic Clinical Cancer Photodetection: Apparatus Design and Preliminary Results," 1997, Journal of Fluorescence, vol. 7, No. 1, pp. 75-83.

Williams, Jim, "Practical Circuitry for Measurement and Control Problems, Circuits Designed for a Cruel and Unyielding World," Aug. 1994, Linear Technology, Application Note 61, AN61-1-AN61-40.

Yankelevich et al., "Design and evaluation of a device for fast multispectral time-resolved fluorescence spectroscopy and imaging," 2014, Rev Sci Instrum, 85(3):0341303,.

* cited by examiner

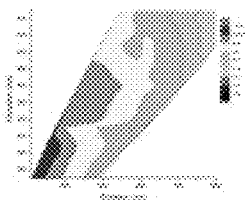 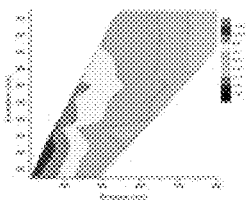 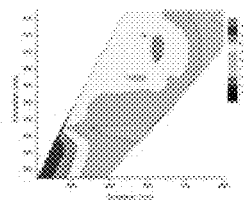 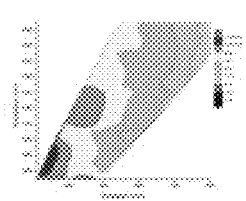
Fig. 7a  Fig. 7b  Fig. 7c  Fig. 7d
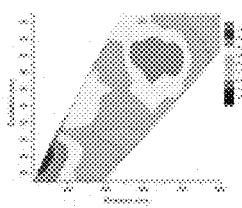
Fig. 7e
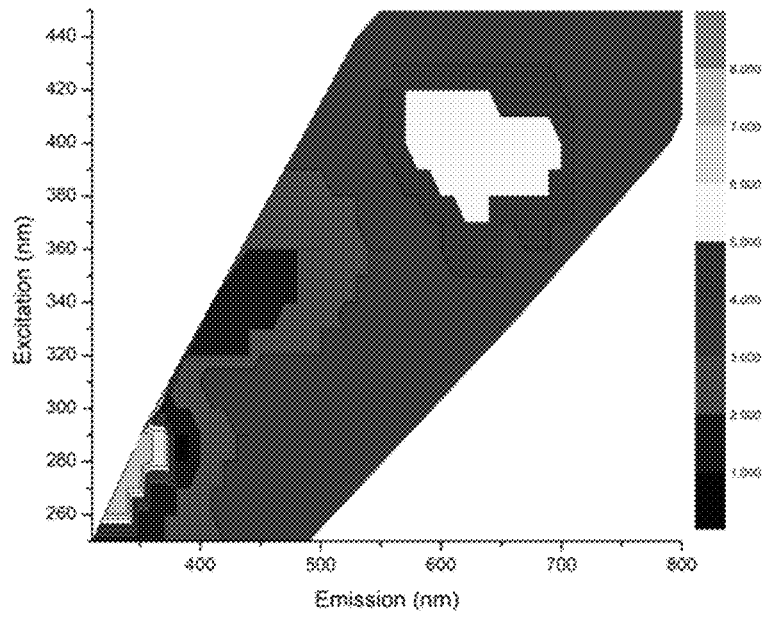
Fig. 7f

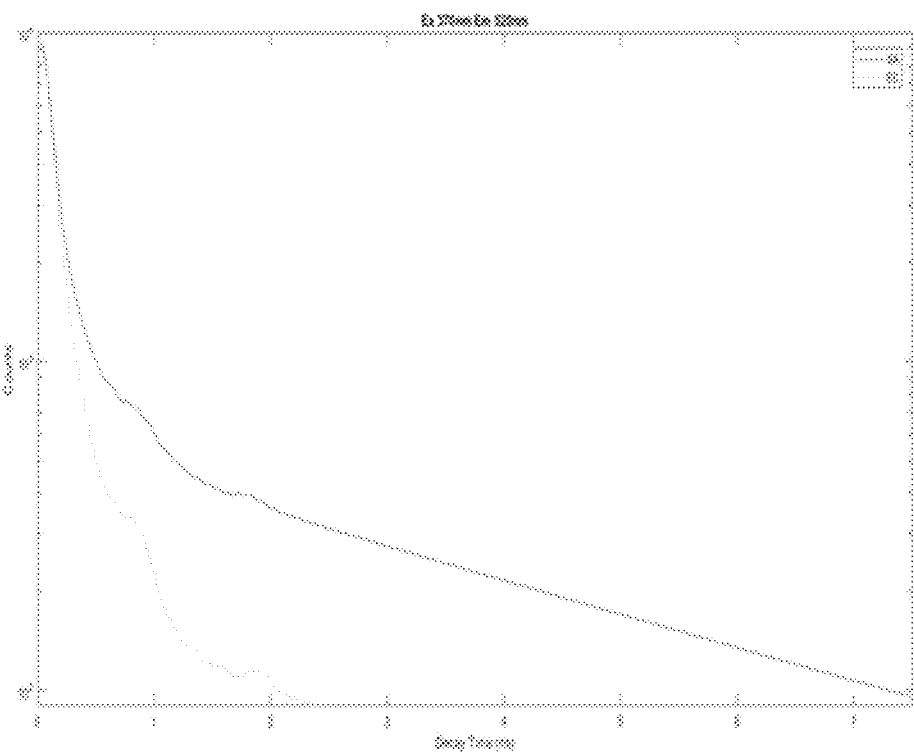
Fig. 15
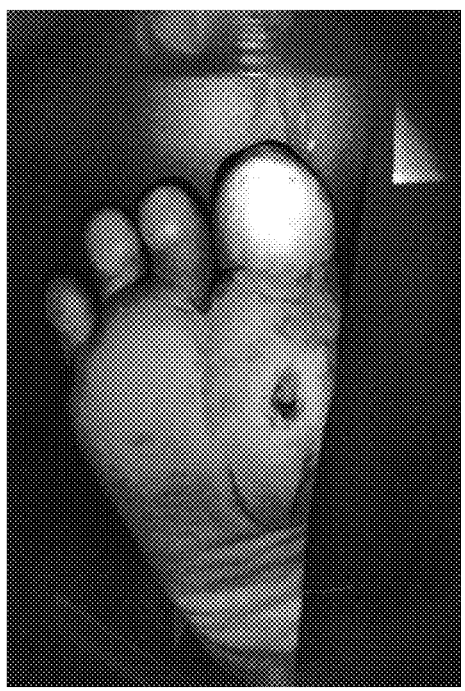 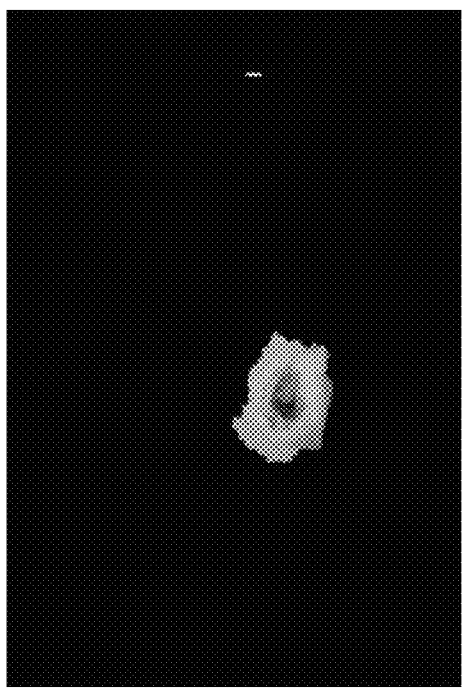
Fig. 16a        Fig. 16b

DEVICE AND METHOD FOR DETECTION AND CLASSIFICATION OF PATHOGENS

PRIORITY AND CROSS REFERENCE TO RELATED APPLICATIONS

This application is the U.S. National Stage Application under 35 U.S.C. § 371 of International Application No. PCT/IN2018/050161, filed Mar. 22, 2018, designating the U.S. and published in English as WO 2018/173073 A1 on Sep. 27, 2018, which claims the benefit of Indian Patent Application No. IN 201741010111, filed Mar. 22, 2017. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present subject matter relates in general to a device and a method for detection and classification of pathogens, and in particular to a device and a method for non-invasive, automatic, in-situ detection and classification of pathogens.

BACKGROUND

Infectious diseases caused by pathogens, such as bacteria, protozoa, virus, and fungi, are generally aggravated in patients with primary diseases, such as diabetes mellitus or AIDS. Prompt identification of the causative pathogen helps in timely treatment and averting fatalities. Traditional methods of pathogen identification based on morphology and biochemical tests include cultures, DNA-based methods, and anti-body based detection. Other techniques of pathogen identification include Polymerase Chain Reaction (PCR), Raman and Fourier Transform Infrared (FTIR) spectroscopy, and the like.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

FIG. 7 illustrates self-organizing maps constructed from the Excitation Emission Matrix Spectroscopy (EEMS) spectra of: (a) *Candida* species other than *Candida albicans* (b) *Candida albicans* (c) *Escherichia coli* (d) *Pseudomonas aeruginosa* (e) *Staphylococcus aureus* (f) combination of (a)-(e), in accordance with an implementation of the present subject matter.

FIG. 15 depicts fluorescence lifetime measurement of *Staphylococcus aureus, Escherichia coli* at 370 nm excitation, in accordance with an implementation of the present subject matter.

FIG. 16 depicts (a) white light imaging and (b) image segmentation on a wound based on white light imaging, in accordance with an implementation of the present subject matter.

DETAILED DESCRIPTION

Figure 1:
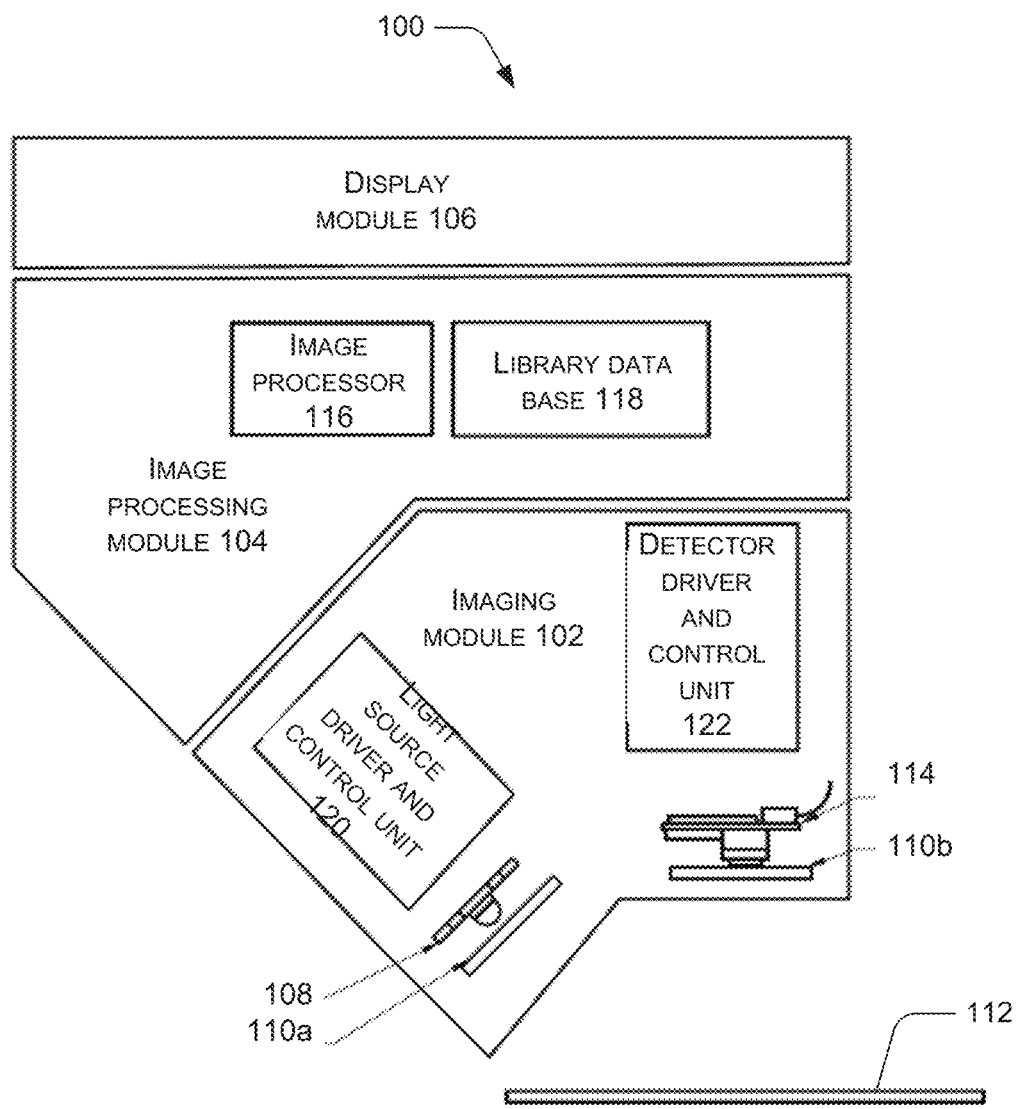
FIG. 1 depicts a schematic representation of a device for detection and classification of pathogens, in accordance with an implementation of the present subject matter.

The present subject matter provides a device and a method for non-invasive, automatic, in-situ detection and classification of pathogens.

Mild infections caused by pathogens may be aggravated in patients with diseases and disorders, such as Acquired Immunodeficiency Syndrome (AIDS) and diabetes. Typically, such mild infections may also become fatal if the causative pathogen is not detected rapidly. Morphological and biochemical tests for pathogen detection, such as bacterial cultures, DNA-based methods, anti-body based detection are laborious, time consuming, and reagent intensive. Molecular methods such as Polymerase Chain Reaction (PCR) are fast and accurate, but are expensive. Raman and Fourier Transform Infrared (FTIR) spectroscopy are efficient methods, but need expensive equipment and skilled operators. Further, pathogens, such as fungus, are difficult to culture and, therefore, require intense skill and facilities. Generally, to control the infection and due to time constraints associated with the abovementioned techniques, empiric antibiotic therapy is often initiated prior to pathogen identification. This may lead to antibiotic resistance and other related medical complications.

Few devices to detect bacteria and fungus non-invasively based on auto-fluorescence property of the pathogens when excited with an Ultra-Violet (UV) light have emerged. However, these devices use steady state fluorescence. Steady state fluorescence generally does not provide specificity to distinguish different pathogens, as most pathogens have similar auto fluorescence markers. For example, most bacteria have tryptophan, Nicotinamide adenine dinucleotide (NADH), Nicotinamide adenine dinucleotide phosphate (NADPH), Porphyrin, Flavins, and the like. Only few pathogens have distinguishably different bio-molecules, for example, pyoverdine in case of *Pseudomonas aeruginosa*. Therefore, it is generally not possible to distinguish pathogens with high specificity based on auto fluorescence technique.

In recent times, fluorescence lifetime studies have also been used for detection and classification of pathogens. However, these studies have not been carried out in-situ but on pre-prepared blood samples. Therefore, these studies do not take into account, variations owing to environmental conditions, pH, growth phase of the organism, concentration, and the like. In-situ detection and classification of microbes has, therefore, proven to be extremely challenging due to the above-mentioned factors affecting the kinetics of the pathogen. Moreover, they have used the entire spectrum of wavelengths for classification, requiring bulky and expensive instruments. Hence, these methods are not suitable for use in point-of-care devices for in-situ pathogen detection and classification.

The present subject matter provides devices for rapid, non-invasive, automatic and in-situ detection and classification of pathogens, in various example implementations. An example device comprises an imaging module, an image processing module, and a display module. The imaging module comprises a plurality of light sources to emit excitation radiation at a predetermined range of wavelengths. The imaging module also comprises an optical switch to expose a sample comprising pathogens to the excitation radiation for a predetermined duration at a predetermined periodicity. The imaging module further comprises a detector configured to synchronously capture time-resolved fluorescence emission spectra, time-resolved reflectance, and transmittance spectra, at multiple spectral bands from the sample. The image processing module is coupled to the imaging module. The image processing module comprises an image processor to perform spatial and temporal resolution of the time-resolved fluorescence emission spectra, time-resolved reflectance, and time-resolved transmittance spectra to obtain a plurality of spectral parameters. The image processing module further comprises a library database comprising a set of standard spectral parameters identifiable with reference pathogens. The image processing module is to compare each of the plurality of spectral parameters with the set of standard spectral parameters to detect and classify the pathogen. The device further comprises a display module to display a result based on the comparison. The present subject matter further provides a method for detection and classification of the pathogens.

The device may be portable and may be a hand-held device. The devices and methods provide a non-invasive, automatic and in-situ detection and classification of pathogens. As used herein, it will be understood that in-situ refers to the detection of pathogens in the sample of a source without any prep-processing of the sample. For example, the sample may be a blood sample or air sample or the like. The device can also be used to detect pathogens in a wound on a body site and such a wound may also be referred to as a sample.

As the device operates based on obtained time-resolved spectroscopy of pathogens using a combination of time-resolved fluorescence spectra and time-resolved reflectance, and time-resolved transmittance spectra, biomarkers associated with various clinically relevant pathogens may be distinguished based on their signature/characteristic spectral parameters extracted from their time-resolved fluorescence spectra and time-resolved reflectance, and time-resolved transmittance spectra, at various designated spectral bands. Further, unlike bulky spectroscopes currently available, the device may be fabricated as a hand held, compact, lightweight, and, therefore, is user-friendly to the clinicians.

Various example implementations and applications of the devices and methods of the present subject matter have been described herein for illustration purposes. It will be understood that the application of the devices and methods is not restricted to these examples. Further, in different applications, the devices and methods may provide some or all of the advantages disclosed herein and it will be understood that, depending on the implementation, the devices and methods may provide different advantages also.

For example, the device can be integrated into normal clinical procedures and can be used in telemedicine and tele healthcare. Further, most of the clinically relevant pathogen may be detected and classified in a few minutes. Further, data acquisition and analysis may happen automatically. Therefore, the device can be operated easily without requiring skillful technicians. This feature helps in quickly deciding the treatment protocol. The device may also be used for detection and classification of pathogens in resource scarce settings.

The device of the present subject matter may be used for quantification of various pathogens present in the sample. The intensity and time dependent fluorescence information at various spectral bands may be obtained from the sample and compared with the fluorescence intensity data from the library database for intensity quantification. The device may also be used for monitoring wound healing and wound closure. The device may also be used to study wound parameters, such as wound size, wound depth, wound temperature distribution, tissue classification, biofilm information, degree of contamination, tissue oxygenation and blood flow.

The device may also be used to study anti-microbial susceptibility by observing and analyzing the spectra by exposing the sample to various antibiotics. For example, the device may be used to study bacterial grown on antibiotics, and corresponding biomarker signatures may be recorded. This information may be used to obtain information on the antibiotics to be prescribed based on the antimicrobial susceptibility of the particular bacteria. It is to be understood that antimicrobial susceptibility of other pathogens, such as fungi, may also be studied. Further, dose and concentration of antibiotics can also be decided based on dilution factors, to determine the dosage of the antibiotics or antifungals to be given.

The device may be configured to study biomolecular composition of various pathogens and their kinetic behavior based on their fluorescence signatures. The device may also be used to in cosmetology. For example, the device may be used to detect the presence of *Propionibacterium* which causes *acnes*. The device may also be used during tissue grafting to ensure that the tissue is free of pathogens. The device may be used for forensic detection, for example, to detect the pathogens in body fluids such as saliva, blood, mucus, and the like. The device may be configured to study effectiveness of disinfectants on various hospital surfaces such as beds, walls, hands, gloves, bandages, dressings, catheters, endoscopes, hospital equipment, sanitary devices, and the like.

The above and other features, aspects, and advantages of the subject matter will be better explained with regard to the following description and accompanying figures. It should be noted that the description and figures merely illustrate the principles of the present subject matter along with examples described herein and, should not be construed as a limitation to the present subject matter. It is thus understood that various arrangements may be devised that, although not explicitly described or shown herein, embody the principles of the present disclosure. Moreover, all statements herein reciting principles, aspects, and examples thereof, are intended to encompass equivalents thereof. Further, for the sake of simplicity, and without limitation, the same numbers are used throughout the drawings to reference like features and components.

FIG. 1 illustrates an example device 100 for detection and classification of pathogens, in accordance with an example implementation of the present subject matter. In an example, the device 100 is a hand-held device. The device 100 comprises an imaging module 102, an image processing module 104, and a display module 106.

The imaging module 102 comprises a plurality of light sources 108 configured to emit excitation radiation in a predetermined range of wavelengths. The imaging module 102 further comprises an optical switch 110a configured to expose a sample 112 comprising pathogens to the excitation radiation for a predetermined duration and a predetermined desired periodicity.

The imaging module 102 further comprises a detector 114 configured to synchronously capture time-resolved fluorescence emission spectra, time-resolved reflectance, and time-resolved transmittance spectra at multiple spectral bands from the sample 112. The image processing module 104 is coupled to the imaging module 102.

The image processing module 104 comprises an image processor 116 to perform spatial and temporal resolution of the fluorescence emission spectra, reflectance, and transmission spectra to obtain a plurality of spectral parameters. The image processing module 104 also comprises a library database 118 comprising a set of standard spectral parameters identifiable with various reference pathogens. The image processing module 104 is to compare each of the plurality of spectral parameters, in real time, with the set of standard spectral parameters in the library database 118 to detect and classify the pathogens. The device 100 may also comprise a light source driver and control unit 120 and detector driver and control unit 122 for operating and manipulating the light sources 108 and the detector 114.

Figure 2:
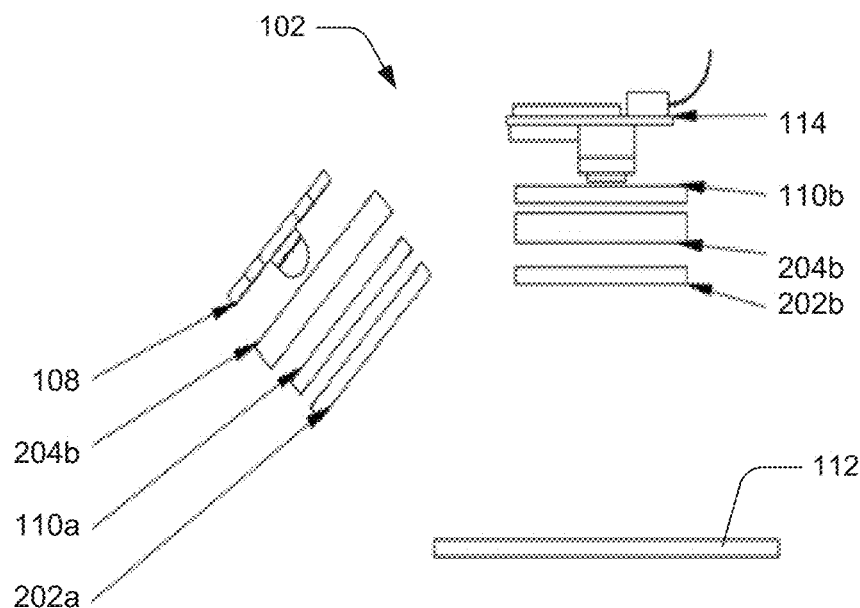
FIG. 2 depicts schematic representation of an imaging module, in accordance with an implementation of the present subject matter.

FIG. 2 depicts schematic representation of the imaging module 102, in accordance with an implementation of the present subject matter. As previously explained, the imaging module 102 comprises the plurality of light sources 108. FIG. 2 depicts a single light source. However, any number of light sources may be used as will be understood. The kind of light source in the imaging module 102 depend on factors, such as application and range of wavelength required for the application. In an example, the plurality of light sources 108 may be arranged in various geometries and configurations. The plurality of light sources 108 may include but are not limited to: a light emitting diode, a laser, a colored light source, a configurable light source, ambient light, or any combination thereof. Therefore, unlike traditional spectroscopy techniques which require bulky light sources, such as halogen lamps, size of the device 100 may be reduced by using the abovementioned light sources.

In an example, the excitation radiation from the light sources has a wavelength in the range from about 250 nm to about 2500 nm. In an example, the excitation radiation has a wavelength in the wavelength range from about 300 nm to about 1100 nm. Thus, in contrast to typical spectroscopy techniques, the device can include light sources for a specific range of wavelengths, thereby allowing further reduction in device size and enabling it to be made as a handheld device. The excitation wavelength range may be chosen depending on fluorescent characteristics of the biomarkers associated with the likely pathogens contained or to be detected in the sample 112.

In an example, the imaging module 102 further comprises optical components for removing undesired wavelengths of radiation. For example, the imaging module 102 may comprise optical filters, polarizers, optical lenses, mirrors, and homogenizers. FIG. 2 depicts optical lens 202a, 202b, collectively referred to as optical lens 202, and optical filters 204a, 204b, collectively referred to as optical filters 204, coupled both with the light source 108 and the detector 114. It is to be understood that a variety of suitable optical lenses 202, optical filters 204, and a combination of both may be coupled either to the light source 108 or to the detector 114, or to both. In another example, an array of optical filters 204 and optical lenses 202 are included in the imaging module 102 and mechanisms as known in the art may be used for selecting the required optical filters 204 and optical lenses 202.

For example, selection of the optical filters 204 and optical lenses 202 may be achieved manually or automatically. In an example, the optical filters 204 and optical lenses 202 are arranged in a polygonal shape. In an example, a linear optical filter or linear optical lens change mechanism using a linear slider may be used. In another example, circular filter change mechanism may be used, where the optical filters 204 and optical lenses 202 are arranged on a rotatable circular disk which may be moved manually or attached to a servomotor. In this example, the position of the optical filters 204 and optical lenses 202 in front of the detector 114 may be controlled by a smart phone application in order to capture the fluorescence emission spectra at desired spectral bands. In certain embodiments, the optical filters 204 may be configured to capture the emission spectra at the following wavelengths: 415 nm, 470 nm, 515 nm, 560 nm, and 620 nm.

The imaging module 102 further comprises optical switch 110a, 110b, collectively referred to as optical switch 110 which helps in adjusting the periodicity and duration of the excitation radiation onto the sample 112. The kind of optical switch 110 and overall configuration of components selected, depends on application of the device 100. In an example, the optical switch 110 is a pulsed LED control unit that can attain a plurality of pulsing periods and duty cycles. The duty cycle and pulsing period may be provided by a user. A pulse controller may be configured to control an oscillator, Phase Locked Loop, and Pulse Generator Module as provided by the user. The pulse generator and LED driver module drives the LED as per the configuration applied. It is to be understood that based on the predetermine periodicity and duration, either a mechanical switch, an electronic switch, or an optoelectronic switch may be used as will be understood.

In an example, the device 100 may be a smartphone coupled with suitable light sources, optical lenses, and filters where a camera of the device 100 may be used as the detector 114 to capture fluorescence, reflectance and transmitted images. In said example, the smartphone may be coupled to a multi wavelength light emitting diode printed circuit board. A light blocking enclosure may also be attached to the smartphone to minimize interference from the ambient light.

In an example, the detector 114 is to capture emitted and reflected spectra in the wavelength range from about 300 nm to about 4000 nm. Transmitted spectra can be captured if the detector is placed in a transmission geometry, i.e., opposite to light source, instead of reflection geometry (same plane as the light source). In an example, the fluorescence imaging is combined with near infrared (using sources from 650 nm to 2500 nm) and mid-infrared (using sources from 2500 nm to 4000 nm) reflective imaging for monitoring tissue oxygenation and wound healing. Any suitable detector 114 may be used in the device 100 based on the spectral wavelength to be captured. In an example, the detector 114 comprises at least one of the following: a charge coupled device, a complementary metal-oxide-semiconductor camera, an avalanche photodiode, a silicon detector, an indium gallium arsenide detector, an indium gallium arsenide camera, indium antimonide detector, bolometer camera, photomultiplier tube detector, or any combination thereof. Silicon based detectors and cameras are typically used for fluorescence imaging and reflective imaging in the visible range. Indium gallium arsenide cameras and detectors are typically used for near-infrared range and indium antimonite and bolometers are used for mid infrared range. Avalanche photodiode and photomultiplier tube detector are typically used in applications requiring high sensitivity of detection. The type of detector 114 used although reduces resolution as compared to traditional spectroscopes, however, also helps in reducing bulk and, thereby, provides a device 100 which has a reduced form factor and is portable.

Most pathogens have similar autofluorescence markers (For example: most bacteria have amino acids such as tryptophan, tyrosine, phenylalanine, Nicotinamide Adenine Dinucleotide (NaDH), Nicotinamide Adenine Dinucleotide Phosphate (NaDPH), Porphyrins etc.). Only few bacteria have specific bio-molecules such as pyoverdine (in case of *Pseudomonas aeuriginosa*) and Ptyriolactone (in case of *Malesseciae*). Therefore, the steady state fluorescence emission peaks of some of these biomarkers fall in the same wavelength region. Hence, steady state fluorescence spectroscopy alone is not sufficient to distinguish between pathogens, let alone classifying them. But different pathogens secrete these auto-fluorescence biomolecules of interest, based on their environmental conditions, biochemical pathways, energy-releasing steps, heme acquisition pathways leading to various extracellular siderophore secretions such as enterobactin, rhizobactin, hydroxamates etc. These interactions with environment significantly changes with respect to time. Therefore, time-resolved spectroscopy—both fluorescent and reflection or transmission is a better tool to distinguish between pathogens. The device 100 as disclosed herein for measuring both steady state and time-resolved fluorescence can improve the specificity and sensitivity of detection and pathogen classification accuracy.

The device 100, of the present subject matter, is configured to capture fluorescence spectra from the sample 112 apart from the reflected or transmitted light. In an example, the device 100 is designed to capture time-resolved fluorescence spectra from the sample 112, as steady state fluorescence spectroscopy alone is not sufficient to classify most of the clinically relevant pathogens. However, in some examples, steady state fluorescence spectra may be additionally used for preliminary high-level pathogen classification.

In an example, time-resolved reflected or transmitted spectra combined with time-resolved fluorescence spectra is useful for classification of clinically relevant pathogens. Time-resolved fluorescence spectroscopy may encompass either fluorescence life time spectroscopy or photobleaching spectroscopy or both. Therefore, in the embodiments of the present invention, the device 100 is configured to synchronously capture at least one of the following data from the sample: steady state fluorescence spectra, fluorescence lifetime spectra, or photobleaching spectra along with time-resolved reflectance and time-resolved transmittance spectra.

In the example where the device 100 is to obtain fluorescence life time spectra of the sample 112, the excitation radiation has the predetermined duration in the range from about 1 ps to about 1 s and the predetermined periodicity in the range from about 0.01 ns to about 1 s. In another example, where the device is or photobleaching spectra, the excitation radiation has the predetermined duration in the range from about 1 ms to about 10 s and the predetermined periodicity in the range from about 0.01 s to about 1 min.

These periodicities and durations of excitation radiation can be achieved by the selection of appropriate optical switches 110.

For fluorescence life time spectroscopy, the sample 112 is exposed to pulses of excitation radiation, at a particular excitation wavelength (periodically) and the emitted fluorescent spectra is captured at different time instances (enabled by the optical switch 110 coupled to the detector 114) at various spectral bands. This may be done at two or more excitation wavelengths based on the pathogens that need to be classified and the accuracy of the result required. This way, the kinetic fluorescent behavior of various biomarkers associated with the multiple pathogens, that are present in the sample 112 may be captured.

For photobleaching spectroscopy, the sample 112 is excited at a particular excitation wavelength for a particular duration (enabled by the optical switch coupled to the light source) and the emitted fluorescent spectra is captured at different instances within that duration (enabled by the optical switch 110 coupled to the detector 114) at various spectral bands. This may be done at two or more excitation wavelengths based on the pathogens that need to be classified and the accuracy of the result required. This way, the photobleaching behavior of various biomarkers associated with the multiple pathogens, that are present in the sample 112, may be captured.

In the embodiments of the present invention, the image processing module 104 is coupled to the imaging module 102 and works simultaneously to process the images received from the imaging module 102. The image processor 116 is to perform spatial and temporal resolution of the emission and reflectance or transmission spectra from the sample 112. The spatial resolution of the spectra is useful in extracting the spatial distribution of the pathogens in the sample 112. The temporal resolution of the spectra is useful for extracting the time-dependent fluorescence of the pathogens. The spatial resolution is determined by the imaging module 102 and can be tuned as per the application. Similarly, temporal resolution is determined by the optical switch 110 and can be tuned depending on the application. In an example, the resolution of the device 100 is in a range of 1-2 nm based on the application. As the resolution required for the detection and classification of pathogens is low, the bulk and form factor of the device 100 is also lower compared to traditional spectroscopes. The bulk and form factor of the device 100 may be reduced by suitably selecting the plurality of light sources, detectors and the other components on the device 100.

In an example, the image processor 116 is to process all of the time-resolved fluorescence emission spectra, time-resolved reflectance and time-resolved transmittance spectra from the sample 112 to obtain the spectral parameters associated with the biomarkers. In an example, the spectral data collected at various spectral bands from the sample 112 is processed by the image processor 116 and is compared, in real time, against the standard spectral data identifiable with various reference pathogens. The term "real-time" indicates that the comparison occurs immediately after the sample 112 is exposed to the excitation radiation and the detector 114 obtains the spectra. Hence, the comparison can be performed at the point of use of the device 100 and results of the comparison can be obtained in a few minutes rather than few hours or days as typically required.

In one example, the image processor 116 processes the spectral data to extract certain critical spectral parameters that may be useful in distinguishing the various clinically relevant pathogens. In an example, the plurality of spectral parameters comprises at least one of the following: ratios of amplitude of fluorescence emission spectra, ratios of amplitude of reflectance spectra, ratios of amplitude of transmittance spectra, bandwidth of the fluorescence emission spectra, full width half maxima of the fluorescence emission spectra, or any combination thereof. Amplitude and spectral bandwidth parameters in various spectral bands are extracted using standard signal/image processing techniques as will be understood. Fluorescence and photobleaching lifetimes and relative amplitudes are extracted using multi-exponential fit to the obtained intensity values from the detector 114.

In one example, experiments may be initially conducted on pathogens present in various in-situ pathogen infected samples and a set of standard spectral parameters identifiable with various reference pathogens have been captured and may be stored in the library database 118. The term "in-situ" herein refers to untreated sample. Therefore, for detection and classification of the pathogens, the sample 112 is not subjected to any processing or treatment, thereby, reducing time consumption and requirement of skilled labor.

In an example, the library database 118 comprises at least one of the following: excitation emission matrix spectra, excitation emission matrix fluorescence spectra, reflectance spectra, transmittance spectra, fluorescence life times, photobleaching times, absorption coefficients, reflection coefficients, transmission coefficients, scattering coefficients, normalized intensity data, intensity ratios and different excitation and emission wavelengths or any combination thereof, identifiable with various reference pathogens.

In the image processing module 104, each of the spectral parameters extracted from the image processor 116 is compared, in real time, with the library database 118 so as to determine whether each of the spectral parameter is identifiable with a specific reference pathogen contained in the library database 118. In an example, the comparison is based on a first image processing model provided in the library database 118. The first image processing model is obtained based on the set of standard spectral parameters identifiable with reference pathogens.

In an example, the image processing module 104 uses machine learning algorithms for updating the first image processing model to a second image processing model library database 118. Machine learning algorithms helps in automated data capturing and analysis. Machine learning algorithms typically enhances the specificity and accuracy of classification achieved by the device 100.

In an example, a machine learning approach is followed to build and update the pathogen detection model. In said example, features are extracted prior to starting the analysis. In one instance, the features include excitation wavelength, emission wavelength, time dependent fluorescence emission wavelength, and amplitude. Typically, both decay rate and emission peak position changes with respect to time. The extracted features are obtained from a reference database comprising excitation wavelengths, emission wavelengths, time and amplitude of the emitted signal which also include ratio of different emission peaks on multi-wavelength excitation, time dependent fluorescence response of biomolecules and their ratios. In an example, these extracted features are transformed into principle components using Principle Component Analysis technique as known in the art. In said example, after this analysis, K Nearest Neighbour clustering is used to cluster the transformed data. This may be performed until the model is able to generalize on the data set and is able to detect pathogens with a good degree of specificity and sensitivity. Features related to new pathogens that are detected may be periodically added to the library database 118 to keep the image processing module 104 updated.

Figure 3:
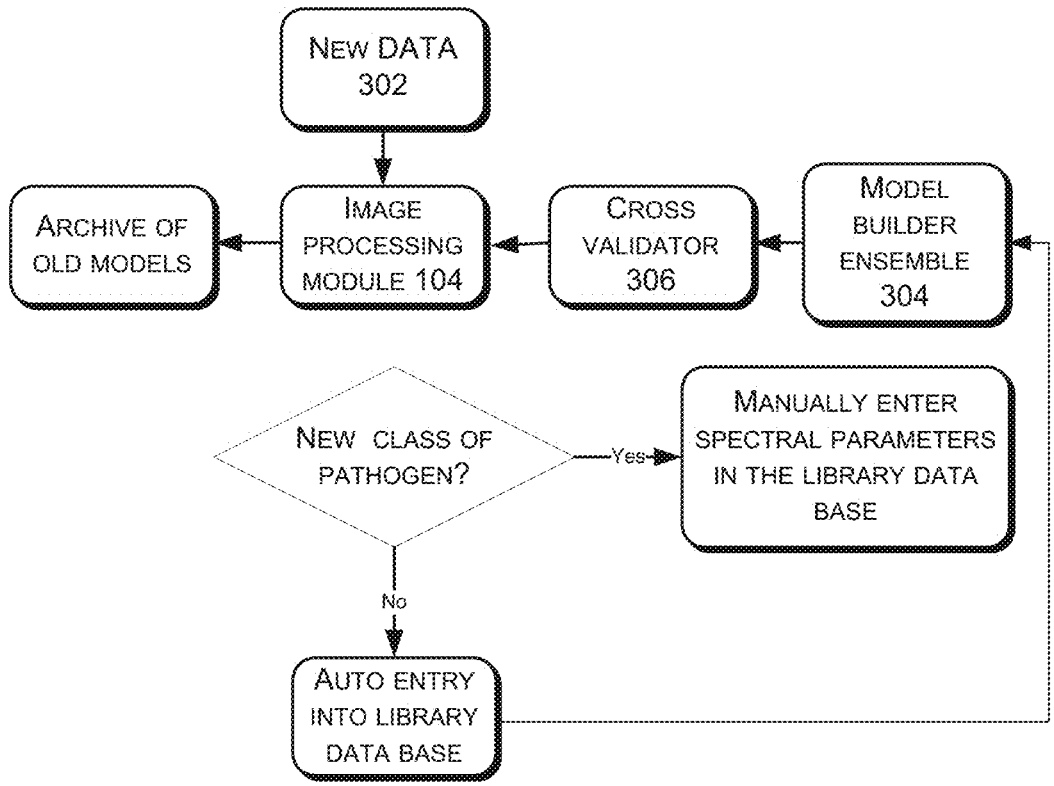
FIG. 3 depicts a method for building a library database, in accordance with an implementation of the present subject matter.

FIG. 3 illustrates an example machine learning approach 300 that is used to incrementally update the image processing module 104 that performs the classification and quantification of a plurality of pathogens. The image processing module 104 comprises a first image processing model to detect pathogens from the reference pathogens based on the comparison as previously explained. The first image processing model may be stored in the library database 118. New data 302 (spatial and temporal fluorescence emission spectra, reflectance and transmittance spectra) is fed into the image processing module 104 to be processed. The new data 302 comprises a new set of standard spectral parameters identifiable with a new reference pathogen. The library database 118 is to receive the new data 102. The image-processing module 104 obtains the plurality of spectral parameters and makes a decision and displays the result. In case the user need to enter a new class of pathogen, it may be done manually.

The plurality of spectral parameters that pertains to the said class also need to be included into the library database 118. A model builder ensemble 304 of the device 100 may read the library database 118 and, subsequently, provides a plurality of image processing models. The plurality of image processing models is provided based on the new set of standard spectral parameters identifiable with the new reference pathogen and the set of standard spectral parameters identifiable with reference pathogen. A cross validator 306 of the device 100 may then use a voting scheme to fix a second image processing model from the plurality of image processing models. The second image processing model is to replace the first image processing model. Using the second image processing model, optimized by machine learning as explained above, the pathogens are subsequently classified.

Any suitable image processor 116 may be used based on the specific computational power and speed required. In an example, the image processor 116 may be at least one of the following: a graphics processing unit, a field programmable gate array, an application specific integrated circuit optimized for a particular target application, a microcontroller unit, a microprocessor unit, a digital signal processor, a single core processor, multi-core processor, system-on-chip processor, multi-spectral camera (where the optical filters at the desired emission spectral bands are monolithically fabricated onto the CCD or CMOS imager) or any combination thereof.

The device 100 of the present subject matter is capable of classifying most of clinically relevant pathogens within a level of accuracy acceptable for various applications. The device 100 is capable of classifying the pathogen based on their family, genus, species and strain level. In an example, the device 100 can be used to distinguish a gram-positive bacterium from a gram-negative bacterium. In another example, the device 100 can be used to distinguish a drug resistant species of bacteria from its other variants. The detection and identification of pathogens happens within a few minutes and the device 100 can be operated easily without much technical training.

The clinically relevant pathogens that may be detected and classified using the device 100, of the present invention include, but are not limited to *Staphylococcus* sp., *Pseudomonas, Escherichia, Candida, Malassezia, Proteus, Propionibacterium, Clostridium, Acinetobacter, Enterococcus, Klebsiella, Streptococcus, Salmonella, Mycobacterium* and *Corynebacterium*. The device 100 may be configured to distinguish between bacteria and fungus, or distinguish within bacteria based on class types into: Actinobacteria, Bacteroidia, Chlamydiae, Bacilli, Fusobacteria, Betaproteobacteria, Gammaproteobacteria, Mollicutes. Fungus may be classified based on the class types into: Ascomycota, Basidiomycota. The classification, can also be based on gram types of bacteria: Gram negative type comprising but not limiting to *Pseudomonas, Escherichia, Klebsiella, Proteus*, Gram positive: *Staphylococcus, Enterococcus, Streptococcus, Corynebacterium*. The classification may also be based on genus: *Corynebacterium, Micrococcus, Mycobacterium, Staphylococcus, Streptococcus, Clostridium, Neisseria, Helicobacter, Enterobacter, Escherichia, Klebsiella, Pseudomonas, Proteus, Salmonella, Mycoplasma*. The classification may also be based on species type comprising but not limited to: *Corynebacterium diphtheria, Mycobacterium tuberculosis, Chlamydia trachomatis, Bacillus anthracis, Enterococcus faecalis, Staphylococcus aureus, Staphylococcus epidermis, Streptococcus pneumonia, Streptococcus pyogenes, Clostridium Difficile, Neisseria gonorrhoeae, Helicobacter pylori, Escherichia coli, Klebsiella pneumonia*. The classification may also depend on the application; in case of disease detection in sputum with respect to Tuberculosis, classification of *Mycobacterium Tuberculosis* species may be of importance, in case of sexually transmitted diseases vaginal swab, *chlamydia* genus may be of interest, in case of Anthrax *Bacillus anthracis* species may be detected, in case of skin infections, *Staphylococcus aureus, Staphylococcus epidermis, Pseudomonas aeruginosa, Streptococcus epidermis, Corynebacterium diphtheria, Proteus mirabilis, Escherichia coli* may needed to be detected and classified. In case of Gastric ulcer detection, *Helicobacter pylori* may be of interest. In case of food contamination, *Salmonella typhi* may be of relevance. In case of urinary infection, *Escherichia coli, Proteus mirabilis, Proteus vulgaris* may needed to be classified. In case of air borne contamination, distinction between bacteria and fungus need to be classified. In case of antimicrobial susceptibility testing, the device 100 may be placed on to an antibiotic coated plate where the sample 112 containing the bacteria may be coated and the device 100 may be used for obtaining the susceptibility pattern.

The device 100 of the present invention is suitable for studying the pathogens present in various kinds of samples 112. The sample may comprise one or more of the following: a body part, a wound, a fluid, a surface, a consumable commodity, a laboratory equipment, a sanitary device, a sanitary equipment, ambient air, a biochemical assay chip, a microfluidic chip, pus, blood, urine, saliva, sweat, semen, mucus, plasma, or any combination thereof for applications ranging from diabetic foot ulcers, surgical site infections, burns, hospital acquired skin and soft tissue infections, dermatology, cosmetology, plastic surgery, infection management in the hospitals, skin diseases, photodynamic therapy monitoring, anti-microbial susceptibility testing.

The device 100 of the present subject matter is automatic, user-friendly and may be seamlessly integrated into the clinical procedure in small clinics, hospitals or at home. The device 100 comprises a display module 106 to display the result, based on the comparison of the detected spectra and the spectra in the database, to the user. Typically, the result comprises at least one of the following: detection of various pathogens presents on the sample, pathogen spatial distribution data, pathogen growth state data, co-colonization data, biofilm information, biomarker information, pathogen quantification data, a treatment protocol, or any combination thereof. The result that is displayed on the screen may also be manipulated by the user, shared and stored for future use and any other further analysis.

In an example, the device 100 further comprises a human machine interface which will comprise of one or more of the following: Light Emitting Diodes, Liquid Crystal Display, Thin Film Transistor Display, OLED (Organic Light Emitting Diode) Display, Capacitive Touch Screen, Resistive Touch Screen, Toggle Switches, Buttons. These digital displays and buttons enables the users to use and manipulate the device easily. The device 100 may be powered by standard AC/DC power sources or batteries. The device 100 may include a software allowing the operator to control and manipulate the device features and modes, store and analyze the data, share or retrieve the data as and when required. The device 100 may be configured for wire or wireless transfer of data. The device 100 may further configured to be interfaced with external device such as a printer, a computer, a tablet, a display unit, or an external hard disc. In an example, the device 100 may be affixed to a robotic arm. In an example, the device 100 is configured for automatic operation. In said example, a positive feedback between the imaging module 102 and the image processing module 104 can be set up that can be utilized to automatically capture the data till identification of most relevant pathogens is achieved to a desired accuracy.

Figure 4:
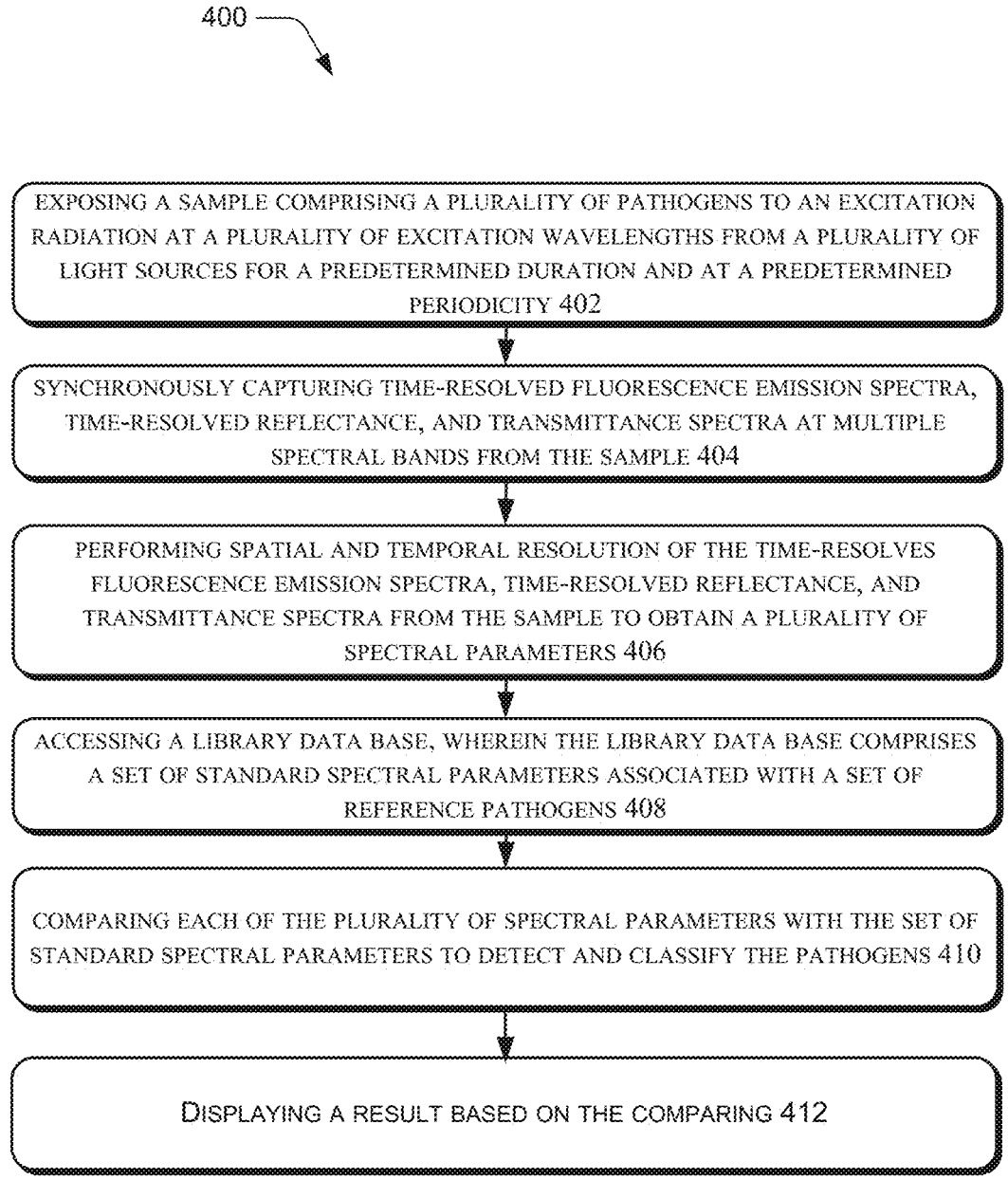
FIG. 4 illustrates a method for detection and classification of pathogens, in accordance with an implementation of the present subject matter.

FIG. 4 illustrates an example method 400 for detecting and classifying pathogens, in accordance with principles of the present subject matter. The order in which the method 400 is described is not intended to be construed as a limitation, and any number of the described method blocks can be combined in any order to implement method 400 or an alternative method. Additionally, individual blocks may be deleted from the method 400 without departing from the spirit and scope of the subject matter described herein. Furthermore, the method 400 may be implemented in any suitable hardware, computer readable instructions, firmware, or combination thereof. For discussion, the method 400 is described with reference to the implementations illustrated in FIGS. 1-2.

A person skilled in the art will readily recognize that steps of the method 400 can be performed by programmed computers. Herein, some examples are also intended to cover program storage devices and non-transitory computer readable medium, for example, digital data storage media, which are computer readable and encode computer-executable instructions, where said instructions perform some or all of the steps of the described method 400. The program storage devices may be, for example, digital memories, magnetic storage media, such as magnetic disks and magnetic tapes, hard drives, or optically readable digital data storage media.

With reference to method 400, as illustrated in FIG. 4, at block 402, a sample comprising a plurality of pathogens is exposed to an excitation radiation at a plurality of excitation wavelengths from a plurality of light sources for a predetermined duration at a predetermined periodicity. In an example, the plurality of light sources is the plurality of light sources 108. The plurality of excitation wavelengths may be obtained by using optical filters 204 and the optical lens 202 as will be understood.

At block 404, time-resolved fluorescence emission spectra, time-resolved reflectance spectra, and time-resolved transmittance spectra at multiple spectral bands are synchronously captured. In an example, the time-resolved fluorescence emission spectra, time-resolved reflectance spectra, and time-resolved transmittance spectra are captured by the detector 114. The term "synchronously" indicates that the capture of fluorescence emission spectra is coordinated with the time of excitation. However, as understood there may be time delay between the excitation and the emission, which si accounted for in the synchronous capture.

At block 406, spatial and temporal resolution of the time-resolved fluorescence emission spectra, time-resolved reflectance, and transmittance spectra is performed to obtain a plurality of spectral parameters. In an example, the spatial and temporal resolution is performed by image processor 116 of the image processing module 104.

At block 408, a library database is accessed. The library database comprises a set of standard spectral parameters associated with a set of reference pathogens. In an example, the library database is the library database 118 of the image processing module 104.

At block 410, each of the plurality of spectral parameters is compared with the set of standard spectral parameters to detect and classify the pathogens. In an example, the comparing is performed by the image processing module 104. At block 412, based on the comparing, a result is displayed. In an example, the result may be displayed by display module 106.

Figure 5:
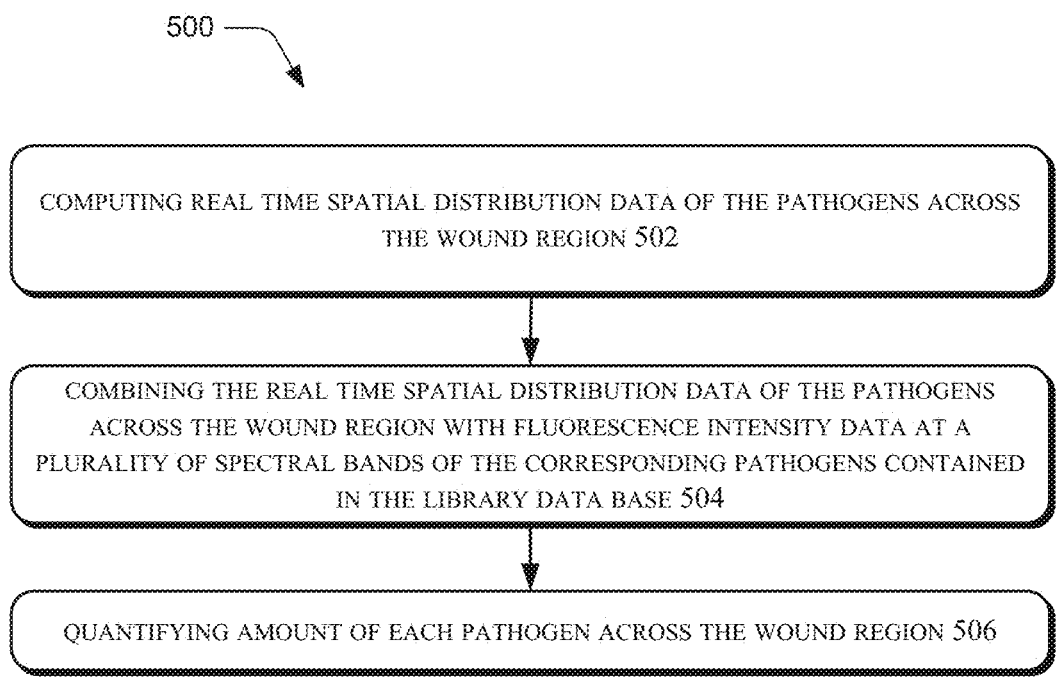
FIG. 5 illustrates yet another a method for detection and classification of pathogens, in accordance with an implementation of the present subject matter.

In an example, the method further comprises steps for non-invasive, automatic, and in-situ wound monitoring. FIG. 5 depicts steps for wound monitoring, in accordance with an implementation of the present subject matter. Subsequent to detection and classification of the pathogens, at block 502, real time spatial distribution data of the pathogens across the wound region is computed. At block 504, the real time spatial distribution data of the pathogens across the wound region is combined with fluorescence intensity data at a plurality of spectral bands of the corresponding pathogens contained in the library database. At block 506, amount of each pathogen across the wound region is quantified. In an example, blocks 502, 504, 506, are performed by the image processing module 104.

The present subject matter will now be illustrated with working examples, which are intended to illustrate the working of disclosure and not intended to be taken restrictively to imply any limitations on the scope of the present disclosure. Unless defined otherwise, all technical and scientific terms used herein have the same meaning as commonly understood to one of ordinary skill in the art to which this disclosure belongs. It is to be understood that this disclosure is not limited to the particular methods and experimental conditions described, as such methods and conditions may vary depending on the process and inputs used as will be easily understood by a person skilled in the art.

EXAMPLES

Example 1: Design and Fabrication of the Device 100

A handheld device was fabricated for in-situ detection and classification of pathogens. The device 100 comprised high power light emitting diodes that are configured to emit light in the following wavelengths: 340 nm, 365 nm, 395 nm. The device comprised of an ARM processor, a 16MP cellphone camera with Sony IMX 398 sensor controlled with an electronic switch that is configured to capture white light and fluorescence images. The device 100 comprised an optical filter change mechanism controlled by a servo motor, and placed in front of the camera that was configured to measure spectral intensity of fluorescence at the following wavelengths: 415 nm, 470 nm, 515 nm, 560 nm, and 620 nm.

The device 100 was enclosed in a compact chassis that is ergonomically stable for use. A trapezoidal ambient light blocking enclosure was attached with the device 100 to prevent ambient light interference, during imaging process. The enclosure also ensures that the user maintains same distance between the sample 112 and the camera to prevent variation in imaging distance. The arrangement of light sources was done in a circular fashion so as to minimize the space and to ensure that all the light sources are equidistant from the camera and are at 45-degree illumination angle to the illuminating surface so as to minimize Rayleigh scattering of the incident light onto the camera. Again, the optical filters were arranged on a circular disk for minimizing the space requirements.

Example 2: Steady State and Time-Resolved Fluorescence Spectroscopic Measurements Steady State and Time-resolved Fluorescence Spectroscopic measurements of clinically relevant pathogens and extraction of relevant spectral parameters by image analysis was conducted.

FIG. 6 shows a steady state fluorescence spectrum obtained for clinically relevant pathogens such as *Candida albicans, Candida* sp., *Pseudomonas aeruginosa, Staphylococcus aureus*, and *Escherichia coli* using RF-6000 Shimadzu Spectro-fluorimeter instrument and raw data of the spectra were collected from LabSolutions RF software. An excitation slit width of 3 nm, emission 5 nm slit width, scanning speed at 600 nm/sec and data points were collected at every 1 nm, sweeping from 200 nm to 450 nm excitation and 200 nm to 800 nm emission. It is known that siderophores are biomolecules secreted by pathogens during iron acquisition mechanism and this is known to cause proliferation and infection.

Figure 6A:
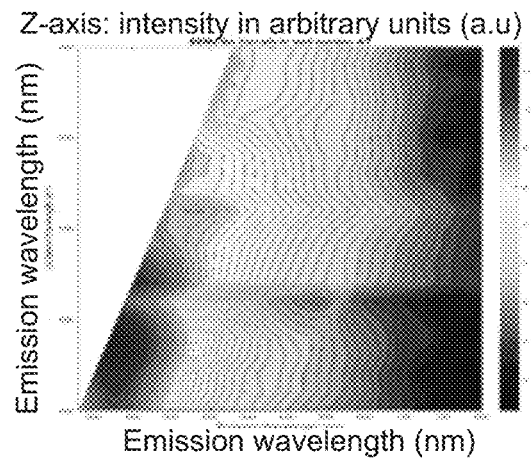
FIG. 6 illustrates excitation emission spectra of: (a) *Candida albicans* (b) *Candida* species other than *Candida albicans* (c) *Pseudomonas aeruginosa* (d) *Staphylococcus aureus* (e) *Escherichia coli*, in accordance with an implementation of the present subject matter.
Figure 6B:
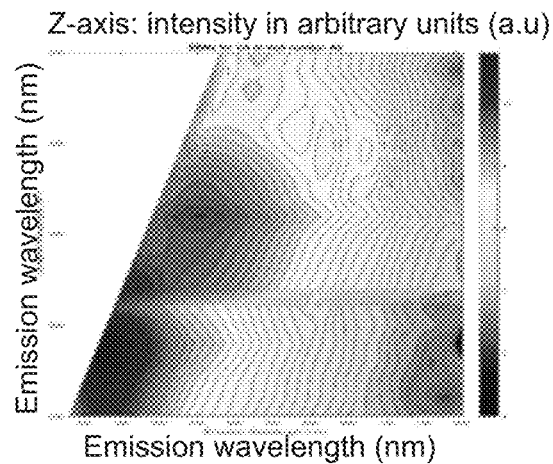
Figure 6C:
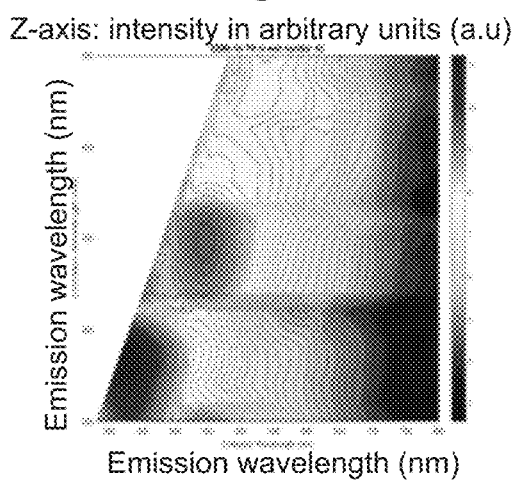
Figure 6D:
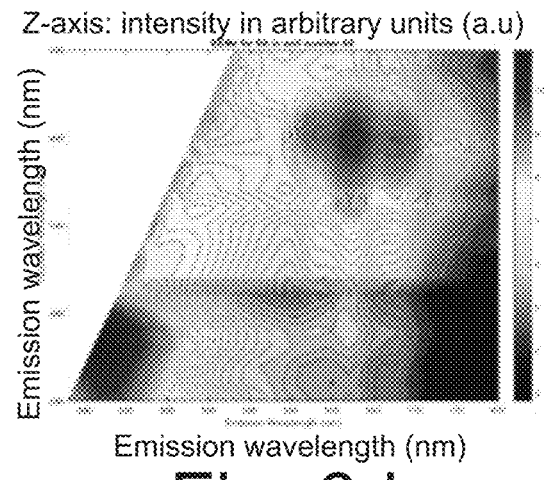
Figure 6E:
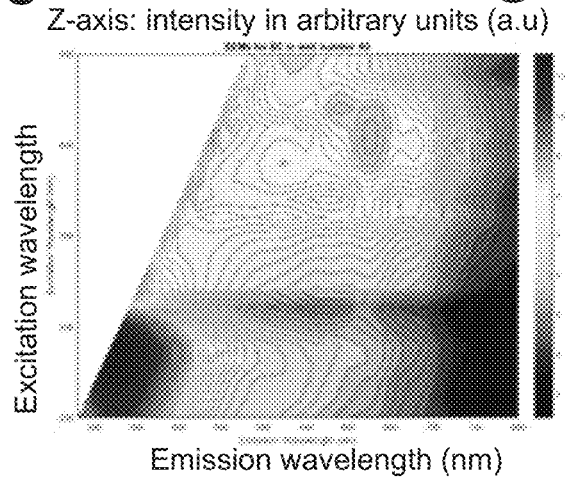

Hence to understand the auto fluorescence characteristics during the iron acquisition, clinically relevant pathogens isolated and sub-cultured from various sources were induced with aminolaevulinic acid, a naturally occurring metabolite in the synthesis of cellular heme, to initiate the iron acquisition pathway. Bacterial species make multiple siderophores. *Escherichia coli* can produce up to four different siderophores (aerobactin, enterobactin, salmochelin, and yersiniabactin). Porphyrin, is a well-known auto fluorescence biomarker that is secreted predominantly by many pathogens during infection. To understand the auto fluorescence property contributed by other siderophores and other biomarkers expressed during growth of the pathogens, excitation emission spectra data was collected using RF6000 Spectro-fluorimeter and a 3D spectra graph was constructed. The bacterial concentration was maintained at 0.5 OD, preprocessed at the log phase of growth to ensure uniform cell density across measurements. This aided in understanding specific excitation, emission wavelengths and the concentration of expression of a biomarker or a combination of them, as an amplitude function. Various spectral parameters, such as excitation wavelength, emission wavelength, emission peak, amplitude at the emission peak, ratio of amplitudes was extracted from the excitation emission matrix spectra. In FIG. 6a, *Candida albicans* does not produce any significant biomarker at 600 nm-650 nm region. *Candida* of other species, produced auto fluorescence at 600 nm-650 nm as shown in FIG. 6b, *Pseudomonas aeruginosa* in FIG. 6c shows a unique peak at 370 nm, 395 nm, 405 nm excitation contributed by siderophore. *Staphylococcus aureus* has distinct porphyrin secretion contribution to high intensity at 600 nm-650 nm as seen in FIG. 6d, followed by *Escherichia coli* in FIG. 6e showing similar property as *Staphylococcus aureus* but moderate intensity porphyrin secretion. Therefore, though same biomolecule were present, difference in composition as a function of amplitude and distinct fluorescence peaks in case of *pseudomonas* was observed.

FIG. 7 shows another statistical method employed to understand the variations in biomarker activity in different pathogens. Self-Organizing Map (SOM), is a neural network model that is based on unsupervised learning. SOM is useful for performing feature dependency extraction from a dataset with unknown dependencies. SOM shows the spectral regions of interest corresponding to auto fluorescence of various biomolecules present in pathogens. The weights obtained from SOM can be used to understand the relative distribution of auto fluorescence biomarkers which can then be used to distinguish pathogens. FIG. 7a-e show relative distribution of auto fluorescence biomarkers in *Candida* sp., *Candida albicans, Escherichia coli, Pseudomonas aeruginosa* and *Staphylococcus aureus* respectively in a color-coded biomolecule classes. FIG. 7f shows the auto fluorescence biomolecules from all pathogen. Further information on individual spectral parameters can be obtained at the excitation wavelength obtained from SOM graph.

Figure 8A:
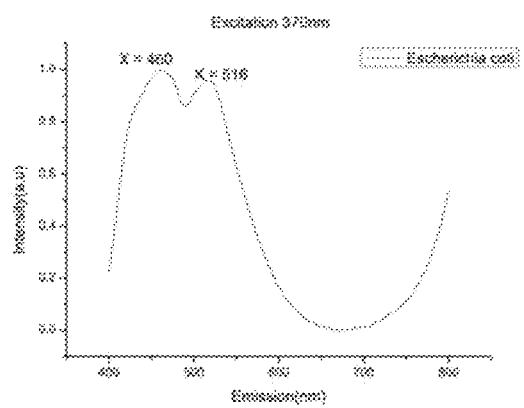
FIG. 8 illustrates fluorescence spectra of: (a) *E. coli*, (c) *Staphylococcus aureus* and (e) *Enterococcus* at excitation wavelength of 370 nm and fluorescence spectra of: (b) *E. coli*, (d) *Staphylococcus aureus* and (f) *Enterococcus* at excitation wavelength of 410 nm, in accordance with an implementation of the present subject matter.
Figure 8B:
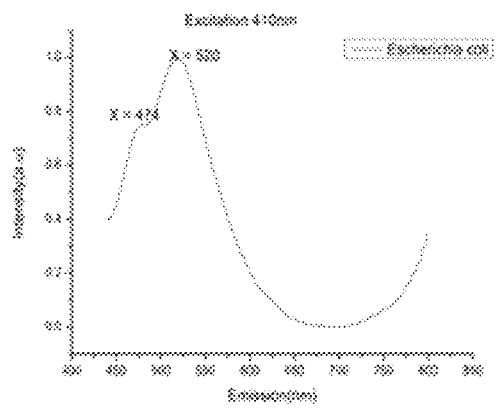
Figure 8C:
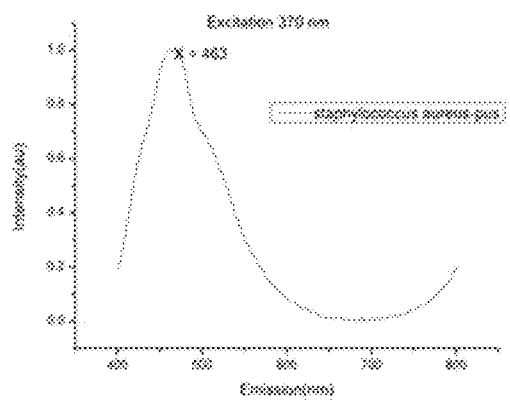
Figure 8D:
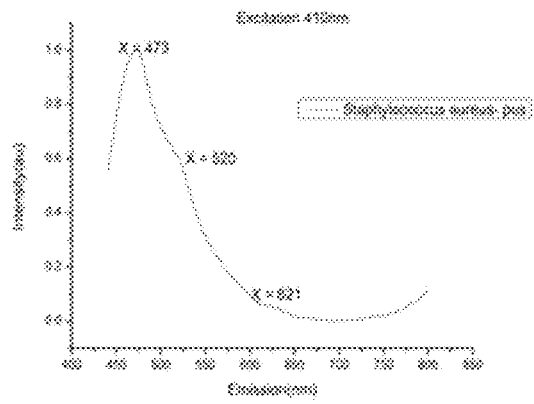
Figure 8E:
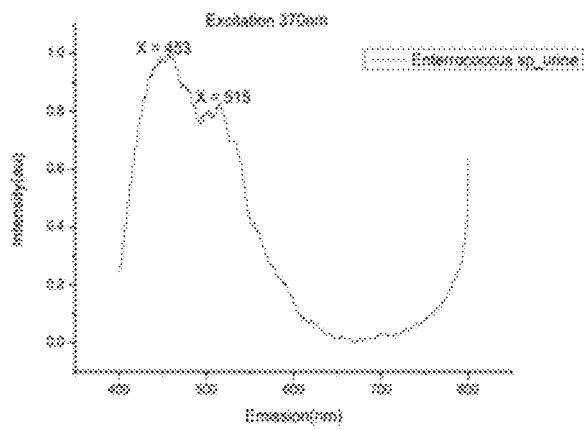
Figure 8F:
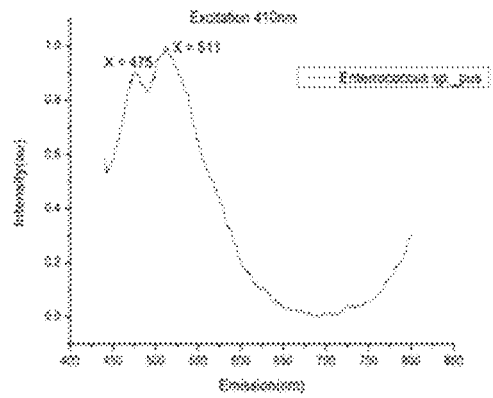
Figure 9B:
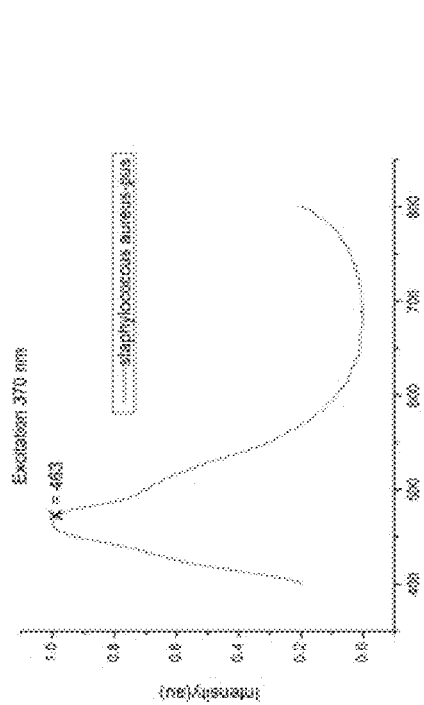
FIG. 9 illustrates fluorescence spectra of *Staphylococcus aureus* sub cultured from (a) sputum, bone tissue, ear swab (b) pus (c) pus (d) sputum, bone tissue, ear swab, in accordance with an implementation of the present subject matter.
Figure 9D:
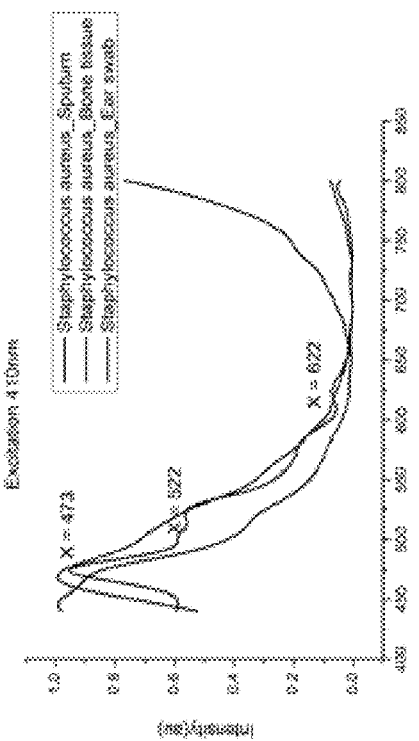
Figure 9A:
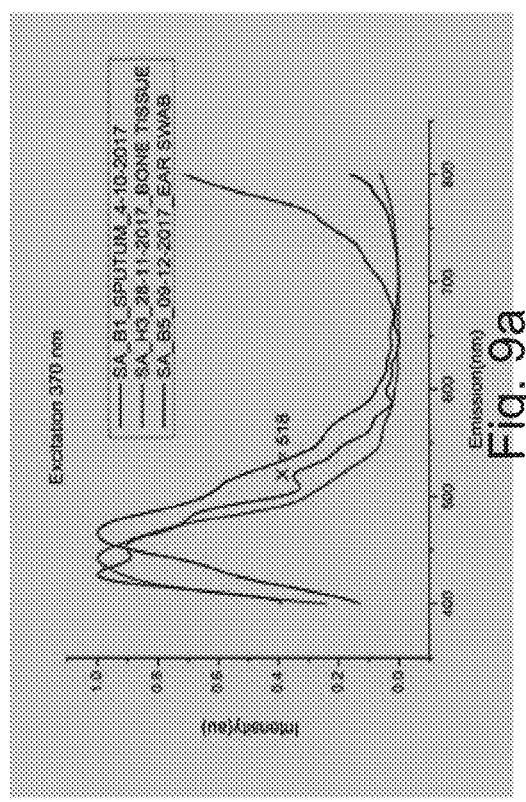
Figure 9C:
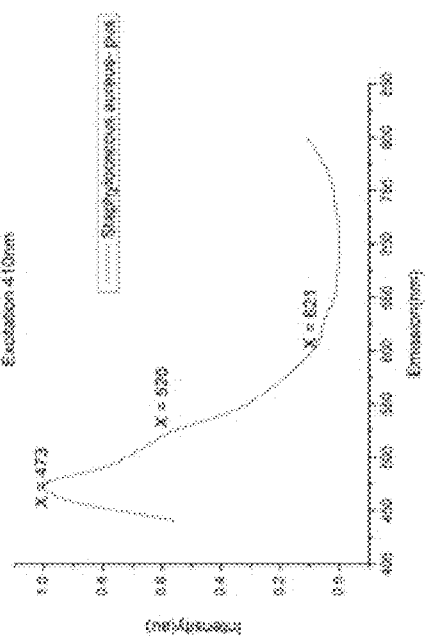

FIG. 8 shows example of 2D fluorescence spectra, of various clinically relevant pathogens such as *Escherichia coli, Staphylococcus aureus, Enterococcus faecalis*. The above pathogens were sub cultured from clinical samples and washed using 9% NaCl, at growth phase and adjusted to 0.5 OD before collecting the spectra. 2D Spectra was collected using SpectraMax i3x Multi-Mode Reader, at gain setting high, and spectra collected at every 1 nm. The 2D spectra gives better understanding on emission peaks and amplitude. FIG. 8a, shows *Escherichia coli* having a double peak on excitation at 370 nm. FIG. 8b shows variation in double peak of *Escherichia coli* at excitation 410 nm. FIG. 8c shows *Staphylococcus aureus* isolated from pus sample, at excitation 370 nm having a single peak at 463 nm emission. FIG. 8d shows *Staphylococcus aureus* at 410 nm excitation and a peak at 473 nm emission. FIG. 8e shows *Enterococcus faecalis* at 370 nm excitation showing a double peak at varying intensity. FIG. 8f shows *Enterococcus faecalis* at 410 nm excitation and corresponding double peak. The spectra gave an understanding of the difference in bio-molecular auto fluorescence. Key spectral parameters, such as double peak emission, intensity data was collected using this experiment, and repeated over many samples, and subcultures isolated in different growth conditions. Excitation emission spectra are similar for *Staphylococcus aureus, Enterococcus faecalis*, and *Streptococcus pyogenes*. Hence, steady state fluorescence alone will not be enough to classify these pathogens, and additional time dependent fluorescence parameters like fluorescence lifetimes, relative amplitudes, photo-bleaching lifetimes are needed to accurately classify pathogens. FIG. 9 is an example of 2D Spectra collected from SpectraMax i3x MultiMode Reader, of clinically relevant *Staphylococcus aureus*, sub cultured and isolated from sputum, bone tissue, ear swab (FIG. 9a and FIG. 9d) at excitations of 370 nm and 410 nm, respectively. 2D Spectra collected from SpectraMax i3x MultiMode Reader, of clinically relevant *Staphylococcus aureus*, sub cultured and isolated from pus, on excitation at 370 nm and 410 nm respectively is shown in FIG. 9b and FIG. 9c. The example shows the variation in auto fluorescence, from biomolecules, with respect to subcultures of the same species isolated from different growth environmental condition.

Figure 10:
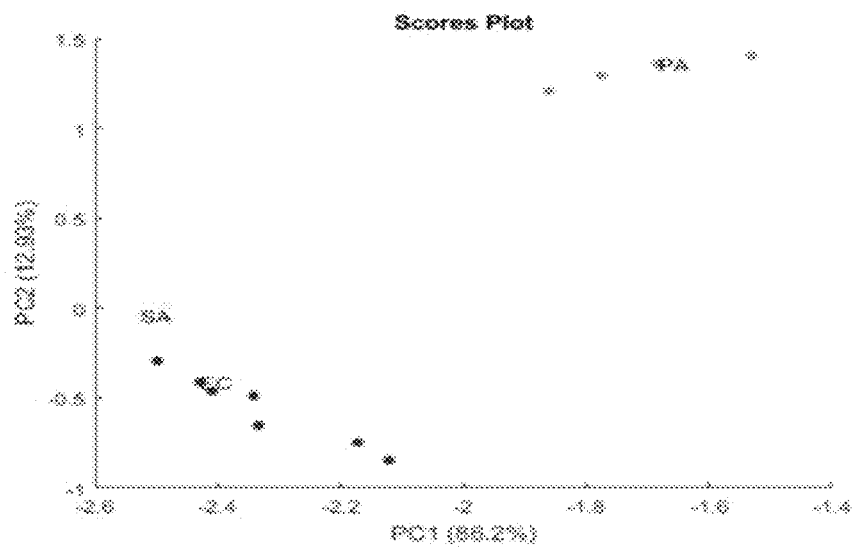
FIG. 10 illustrates Principal Component Analysis of fluorescence spectra of *Staphylococcus aureus, Escherichia coli*, and *Pseudomonas aeruginosa* at 410 nm excitation, in accordance with an implementation of the present subject matter.
Figure 11:
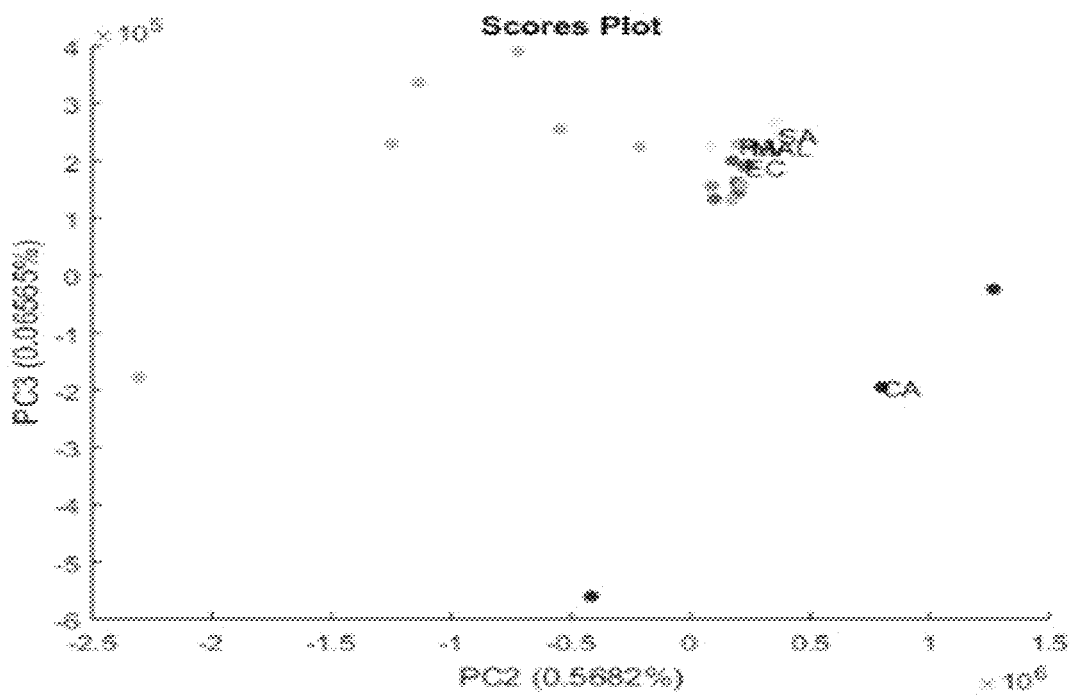
FIG. 11 illustrates Principal Component Analysis of fluorescence spectra *Staphylococcus aureus, Escherichia coli, Pseudomonas aeruginosa*, and *Candida albicans* at 335 nm excitation, in accordance with an implementation of the present subject matter.

FIG. 10 shows a chemometric statistical analysis method, namely the Principle Component Analysis (PCA) to understand maximum separation of bacteria in different excitation wavelengths. Here, PCA at 410 nm excitation on *E. coli, Pseudomonas aeruginosa, Staphylococcus aureus* respectively have been shown, where *Pseudomonas* shows maximum separation at 410 nm excitation. Similarly, PCA at 335 nm shows maximum separation of *Candida* species (FIG. 11).

Figure 12:
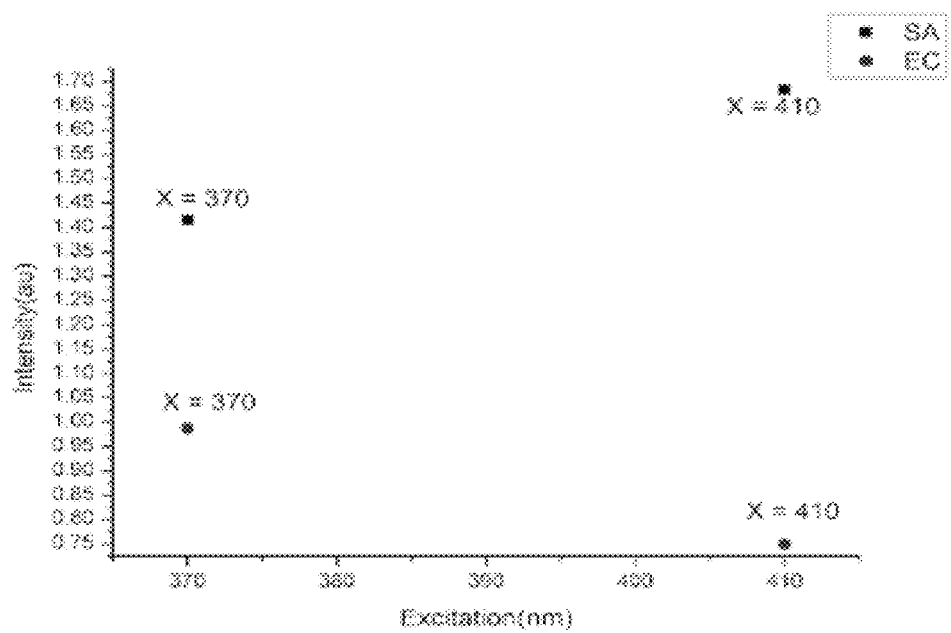
FIG. 12 depicts ratio of the fluorescence emission peaks of *Staphylococcus aureus* and *Escherichia coli* at 370 nm and 410 nm excitation, in accordance with an implementation of the present subject matter.

FIG. 12 shows the ratio of amplitude of fluorescence emission peaks at 370 nm and 410 nm excitation, for *Staphylococcus aureus* and *Escherichia coli*. This example shows that ratio of fluorescence amplitudes in various spectral bands can be effectively used to classify certain pathogens.

Figure 13:
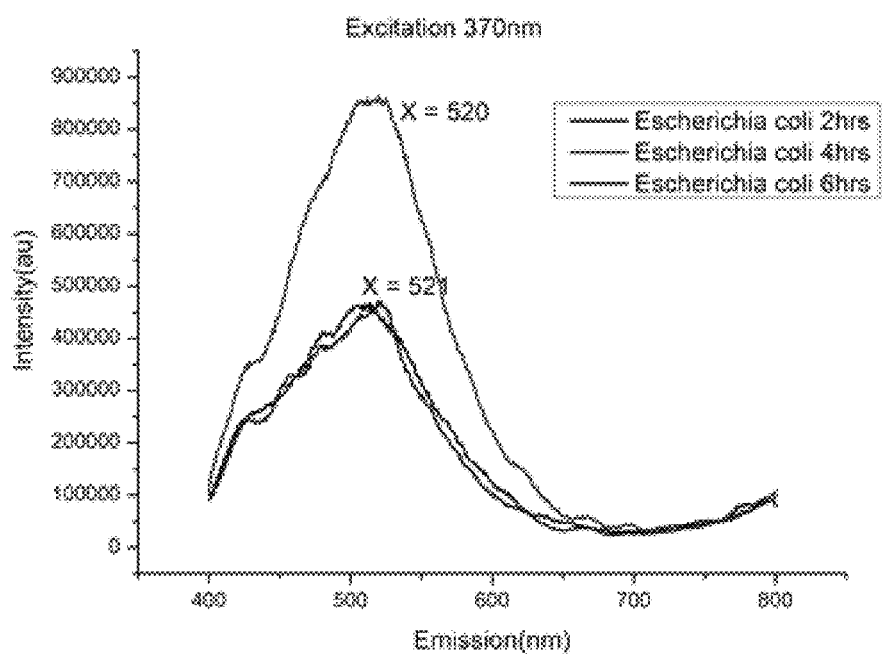
FIG. 13 depicts fluorescence spectra of *Escherichia coli* collected at different growth stages, in accordance with an implementation of the present subject matter.

FIG. 13 shows 2D fluorescence spectra of *Escherichia coli*, collected at different growth stages—2 hours, 4 hours and 6 hours of growth. The bacteria isolated from clinical samples was sub cultured and washed with 9% NaCl for 2D fluorescence spectra measurements using SpectraMax i3x Multi-Mode Reader. It was observed that spectral parameters obtained from steady state fluorescence are not enough for exact classification, mainly because the expression of fluorescence biomolecules depends on various intrinsic factors such as biochemical pathway during an infection and extrinsic factors such as environment, growth conditions, temperature. Therefore, it is clear that additional extraction of time dependent fluorescence parameters was needed.

Figure 14A:
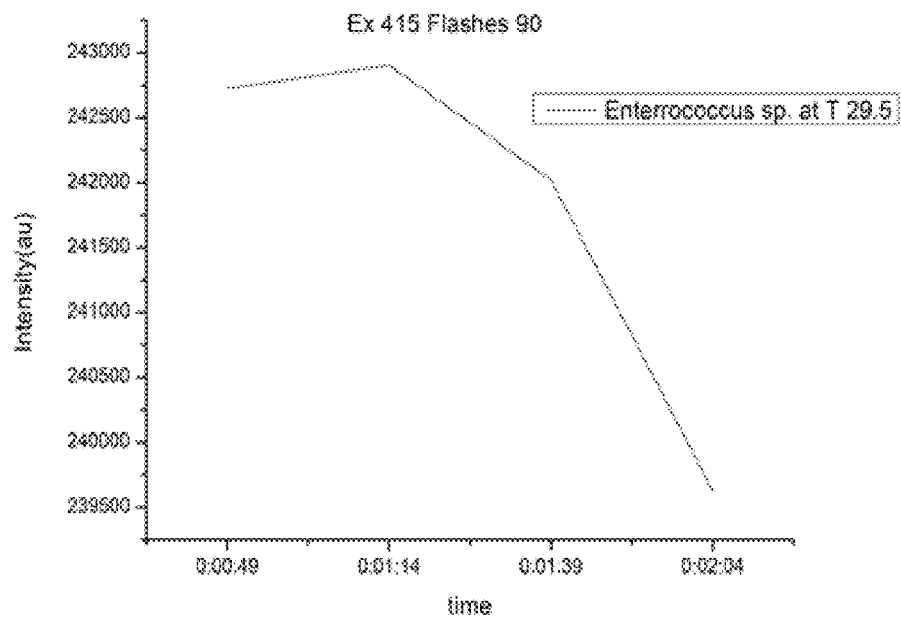
FIG. 14 depicts photobleaching and auto fluorescence changes in (a) *Enterococcus faecalis* and (b) *Staphylococcus aureus*, in accordance with an implementation of the present subject matter.
Figure 14B:
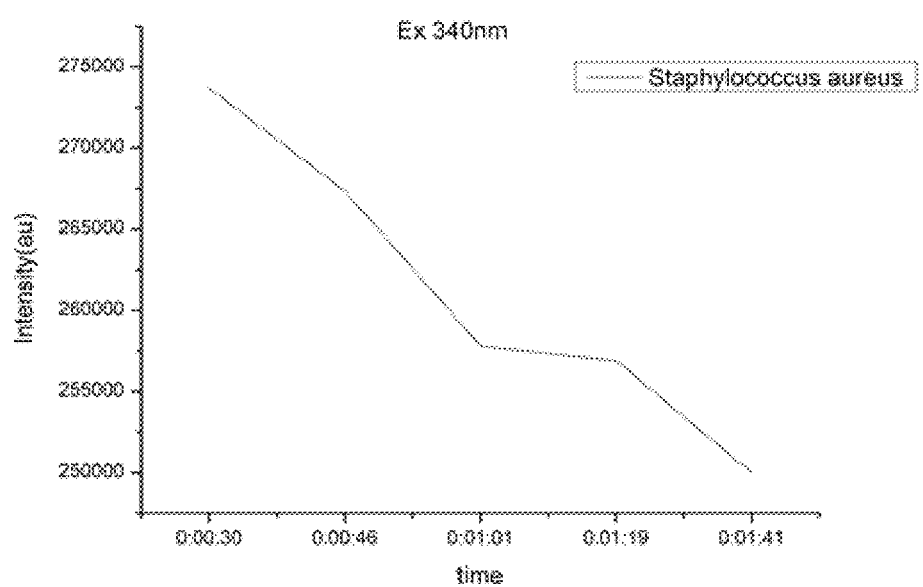

FIG. 14a shows the time resolved fluorescence data contributed due to photo bleaching in *Enterococcus* kept at 29.5 degree. The excitation was at 415 nm (at 90 flashes), and fluorescence recorded at every 49 seconds using SpectraMax i3x Multi-Mode Reader, in the kinetic mode. Similarly, FIG. 14b shows *Staphylococcus aureus* at 340 nm excitation collected at 40 flashes, and recorded every 30 seconds. These graphs show a decrease in fluorescence with time due to photobleaching effect. This is a key spectral parameter that need to be considered for detection and classification of pathogens at genus and species level.

FIG. 15 shows time-dependent fluorescence characteristics of *Staphylococcus aureus* and *Escherichia coli* excited at 370 nm and emission at 520 nm, obtained using Horiba TCSPC instrument (decay recorder was set to 100 ns, the peak count was set to 10000 photons, and each channel duration of 0.027 ns). Though steady state fluorescence spectra are similar at 520 nm corresponding to flavin molecule as shown in FIGS. 8a and 8b, fluorescence lifetimes corresponding to flavins, at 520 nm emission are significantly different for *Staphylococcus aureus* and *Escherichia coli*. This result clearly demonstrates that time-dependent fluorescence can be used to distinguish between certain pathogens that are not possible using steady state fluorescence.

Example 3: Use of Handheld Device of the Present Invention for Various Clinical Diagnostic Applications FIG. 16 shows an example of wound image obtained, by white light imaging, using the device of example 1. Image segmentation was done on the wound image to understand the extent of the wound which was used subsequently for wound healing monitoring. An algorithm was written that could automatically identify the boundary of the wound, based on color parameters, extracted during white light imaging. FIG. 16a depicts white light image of the wound and FIG. 16b depicts segmented image of the wound.

Figure 17A:
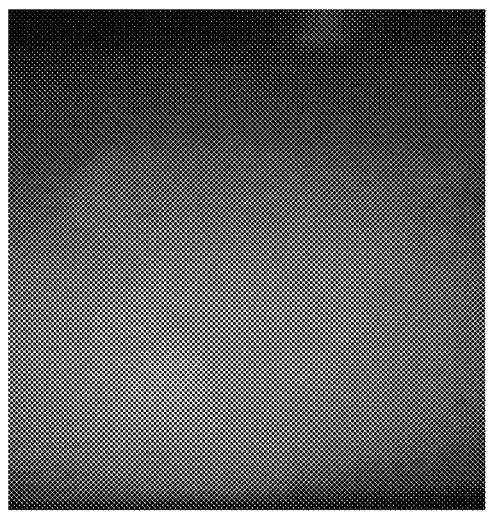
FIG. 17 depicts (a) white light imaging and (b) auto fluorescence imaging on fungus infected hand to identify *Malassezia furfur*, in accordance with an implementation of the present subject matter.
Figure 17B:

FIG. 17 shows white light imaging and auto fluorescence imaging of infected hand to identify *Malassezia furfur*. The images were captured using the device 100 of Example 1, at 365 nm and 395 nm excitation light sources and at 450 nm and 520 nm emission respectively. The auto fluorescence images captured were processed using k-means clustering to clearly elucidate the region of infection and to understand the spatial distribution of fungal infection. FIG. 17a depicts white light image of fungus infected region and FIG. 17b depicts processed auto fluorescence image using k-means clustering to identify the spatial distribution of *Malassezia furfur*.

Figure 18A:
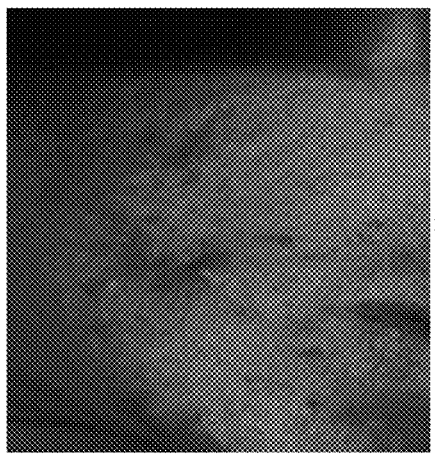
FIG. 18 depicts (a) white light imaging and (b) auto fluorescence imaging showing presence of *Propionibacterium acnes* on the face, in accordance with an implementation of the present subject matter.
Figure 18B:
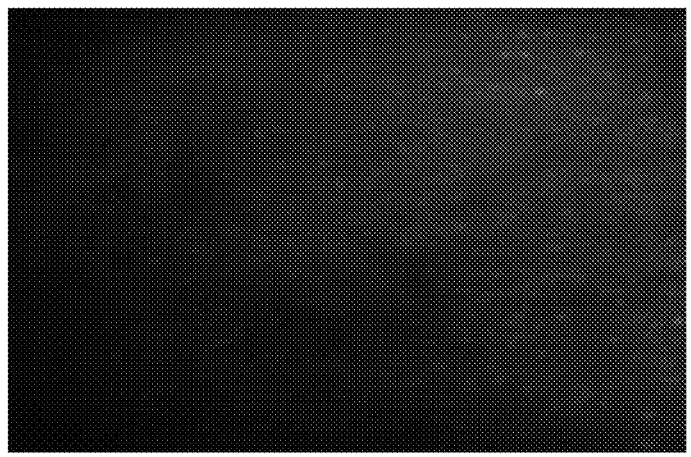

FIG. 18 shows fluorescence image of the face captured using the device 100 of Example 1, at 365 nm excitation and 520 nm and 620 nm emission. The image clearly shows the presence of *Propionibacterium acnes* on the face around the acne region but on within the acne region. This information is vital to understand the extent of infection and helps in optimizing the treatment protocol. FIG. 18a depicts white light image of the face and FIG. 18b depicts fluorescence image of face showing *Propionibacterium acnes* infection around acne region.

Figure 19A:
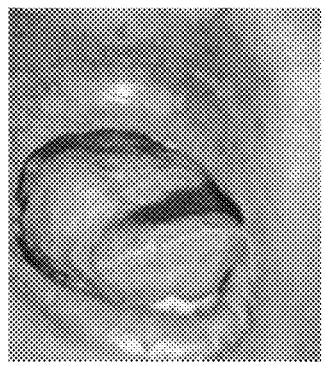
FIG. 19 depicts (a) white light imaging (b)-(c) fluorescence images showing presence of *candida* inside the oral cavity, in accordance with an implementation of the present subject matter.
Figure 19B:
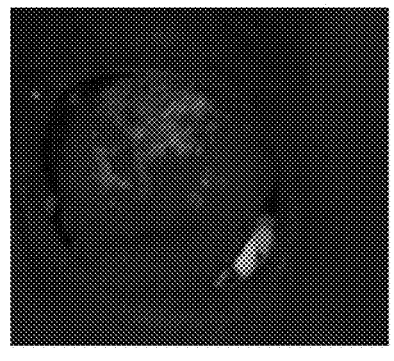
Figure 19C:
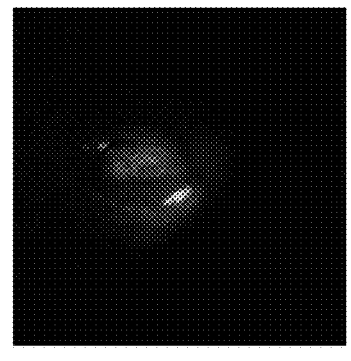
Figure 20A:
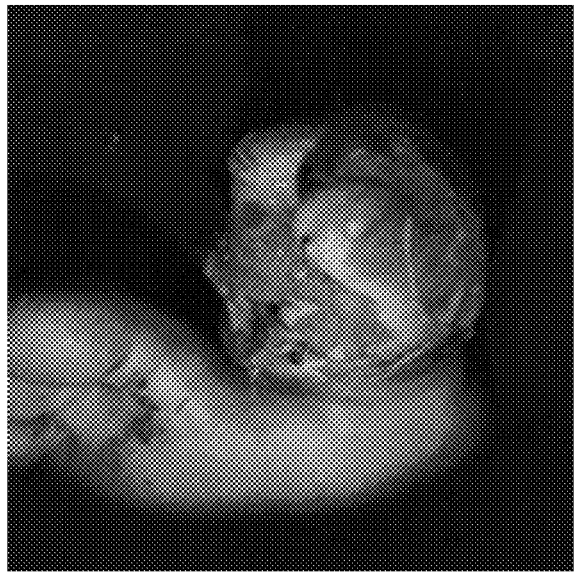
FIG. 20 depicts (a) white light imaging (b)-(d) fluorescence images at excitation 370 nm and 395 nm captured at various spectral bands at 470 nm, 520 nm and 620 nm emission of co-colonization of bacteria on a wound, in accordance with an implementation of the present subject matter.
Figure 20B:
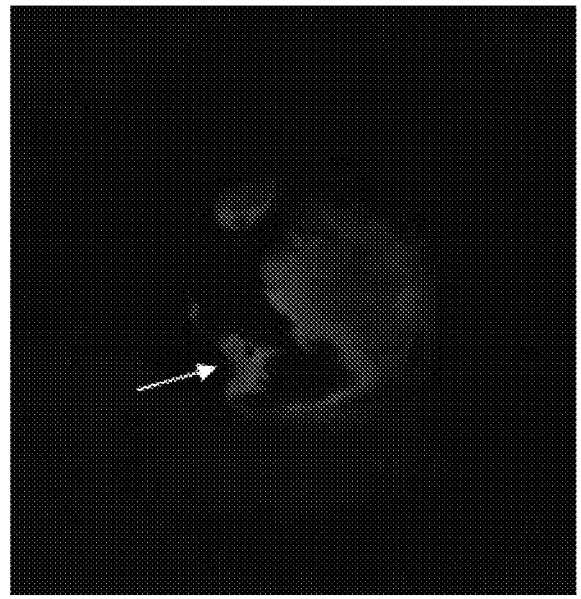
Figure 20C:
Figure 20D:
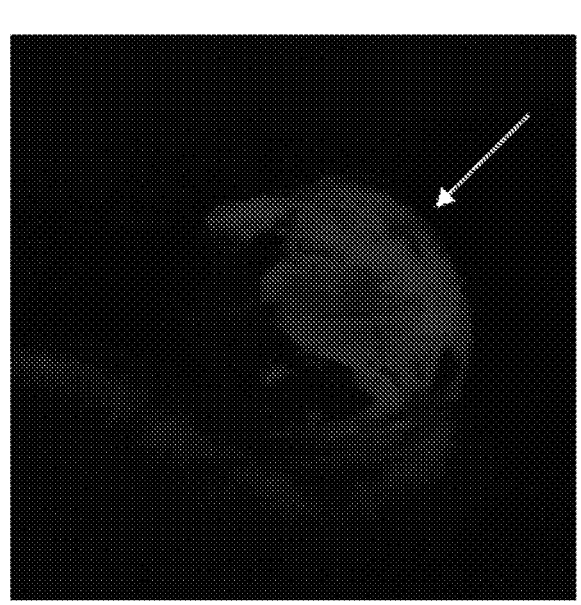

FIG. 19 shows fluorescence imaging of fungal *candida* inside the oral cavity using device 100 of Example 1, at 335 nm and 370 nm excitation and 413 nm and 460 nm emission. k-means clustering is employed to clearly elucidate the region and the extent of infection (FIGS. 19(a) and 19(b)).

FIG. 20 shows fluorescence imaging using device 100 of Example 1. FIG. 20(a) shows the white light image of the wound and FIG. 20(b)-(d) show the fluorescence images at excitation 370 nm and 395 nm captured at various spectral bands at 470 nm, 520 nm and 620 nm emission. The difference in the spatial distribution of fluorescence intensity at various spectral bands was clearly evident. Additionally, some regions (indicated by arrows in FIG. 20(b) and FIG. 20(d)) show more intensity in certain spectral bands clearly demonstrating co-colonization. Understanding the extent and spatial distribution of bacteria co-colonization on a wound is important to tailor the treatment protocol.

Figure 21A:
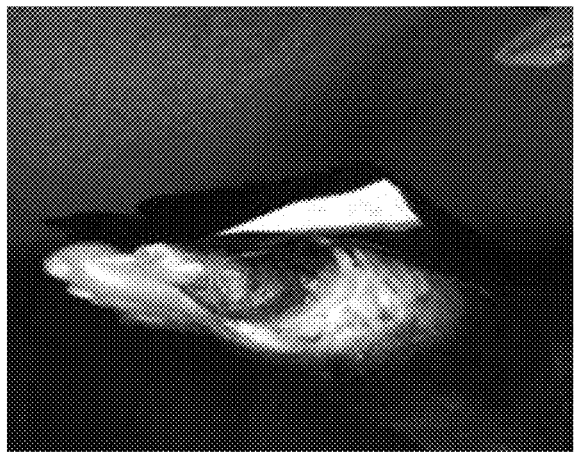
FIG. 21: depicts (a) White light Image and (b) Fluorescent image of a wound using the device, in accordance with an implementation of the present subject matter.
Figure 21B:
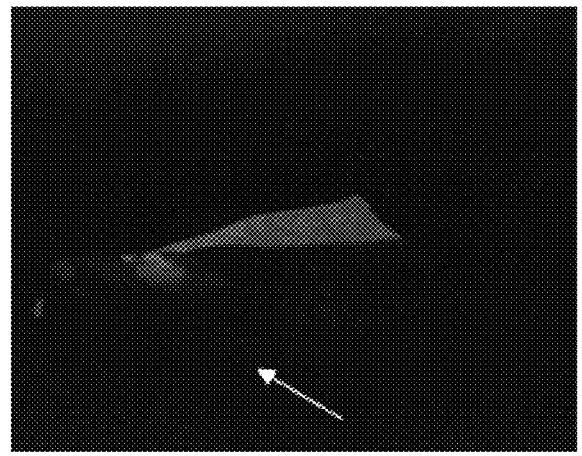

FIG. 21 shows the white light and fluorescence image captured at 370 nm and 395 nm excitation and 470 nm, 520 nm and 620 nm emission using device of example 1. The figure indicates no bacterial colonization on the wound (indicated by the arrow) which is confirmed by the swab culture. (FIGS. 21(a) and 21(b)).

Figure 22A:
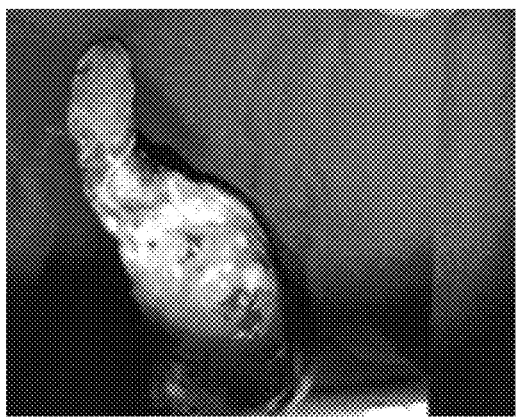
FIG. 22: depicts (a) White light image of a wound, (b)-(d) Fluorescent images of the wound, (e) Fluorescence spectra using the device, in accordance with an example implementation of the present subject matter.
Figure 22B:
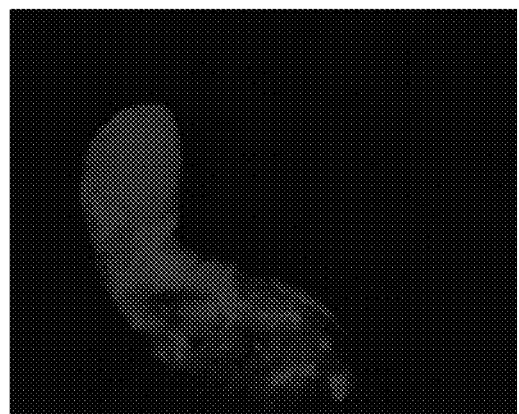
Figure 22C:
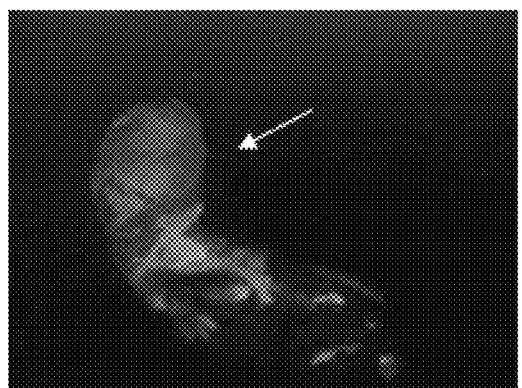
Figure 22D:
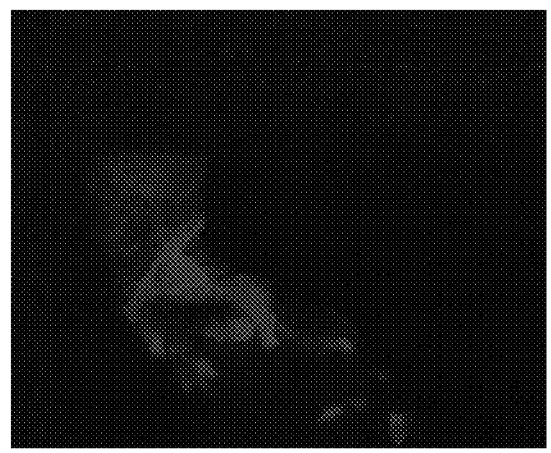
Figure 22E:
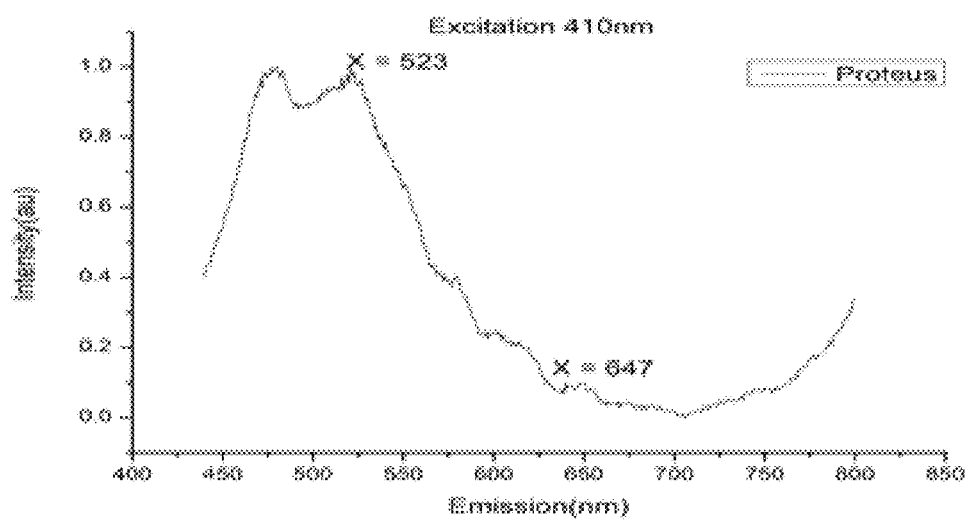

FIG. 22 (a) shows the white light image and fluorescence images (when excited by LED in spectral region 380 nm-410 nm) captured under various emission spectral bands (FIG. 22(b): 470 nm, FIG. 22(c): 520 nm, FIG. 22(d): 620 nm) using device 100 of Example 1. The fluorescence images show the presence of *Proteus* sp. confirmed by swab culture (indicated by arrow in FIG. 21(c) where the swab is taken). Significant fluorescence is present in all the three spectral bands. For comparison, FIG. 22 (e) shows the fluorescence spectra of *Proteus* captured using spectrofluorimeter when excited with 410 nm. Emission at three spectral bands is clearly visible confirming that the fluorescence imaging results matches with the spectral parameters obtained from the graph.

Figure 23A:
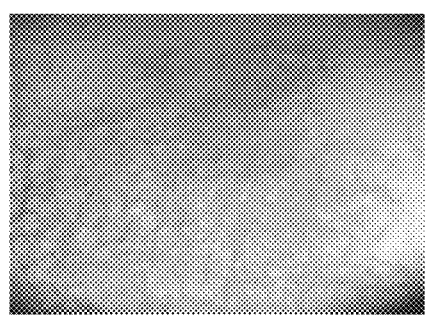
FIG. 23 depicts (a) White light image and (b) color-coded super imposed fluorescence image of dermatophyte fungus using the device, in accordance with an example implementation of the present subject matter.
Figure 23B:

FIG. 23 shows the white light and color-coded super imposed fluorescence image of dermatophyte fungus at 365 nm excitation and 470 nm emission captured using device 100 of Example 1. ((FIGS. 23(a) and 23(b)).

Figure 24:
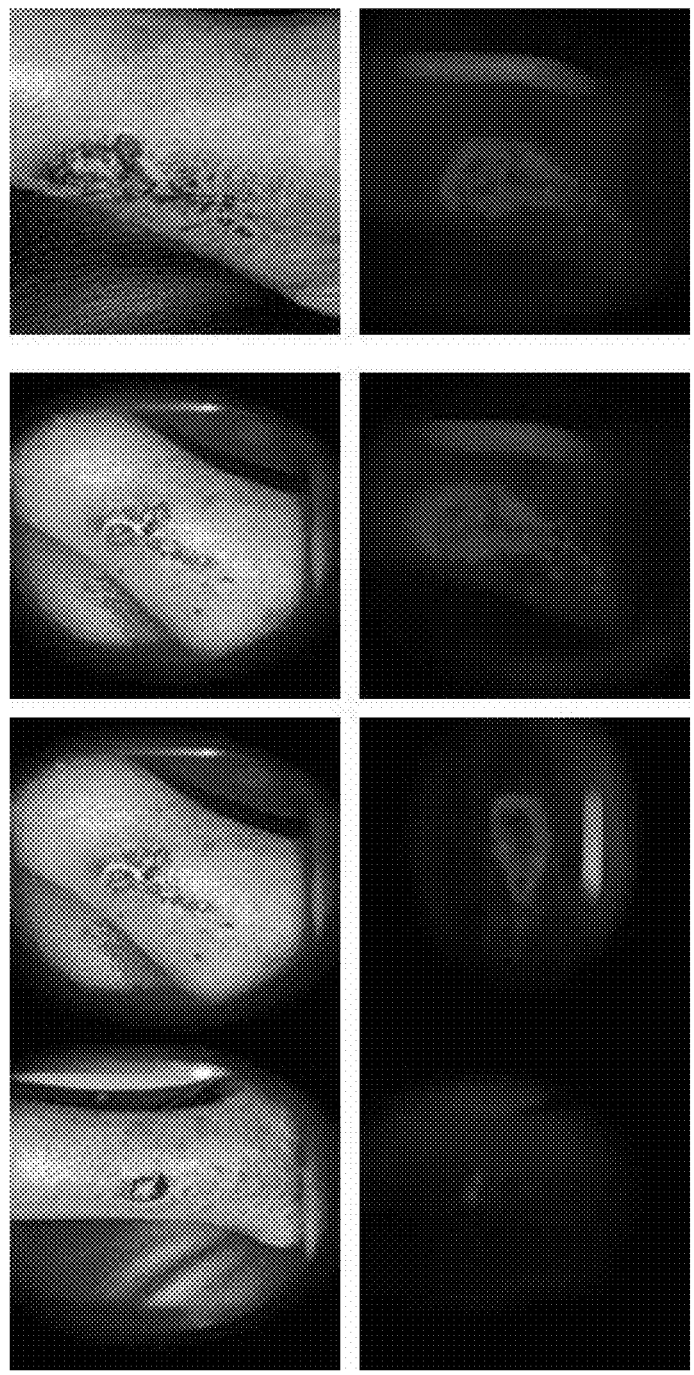
FIG. 24 depicts monitoring of wound over (a) Day 0 (b) Day 2 (c) Day 4 (d) Day 9 using the device, in accordance with an implementation of the present subject matter.

FIG. 24 shows white light imaging (left pictures) and fluorescence imaging (right graphs) of wounds captured on different days (Day 0 to Day 9). The left side white light images clearly showed wound healing over antibiotic administration with time, and corresponding fluorescent images, on the right side, show decrease in bacterial colonies.

Although the subject matter has been described in considerable detail with reference to certain examples and implementations thereof, other implementations are possible. As such, the scope of the present subject matter should not be limited to the description of the preferred examples and implementations contained therein.

What is claimed is:

1. A device for non-invasive, automatic, and in-situ detection and classification of pathogens, the device comprising:
   an imaging module comprising:
   a plurality of light sources to emit excitation radiation at a predetermined range of wavelengths;
   an optical switch to expose a sample comprising pathogens to the excitation radiation for a predetermined duration at a predetermined periodicity; and
   a detector to synchronously capture time-resolved fluorescence emission spectra, time-resolved reflectance, and time-resolved transmittance spectra at multiple spectral bands from the sample;
   an image processing module coupled to the imaging module comprising:
   an image processor to perform spatial and temporal resolution of the time-resolved fluorescence emission spectra, time-resolved reflectance, and time-resolved transmittance spectra to obtain a plurality of spectral parameters; and
   a library database comprising a set of standard spectral parameters identifiable with reference pathogens,
   wherein the image processing module is to compare each of the plurality of spectral parameters with the set of standard spectral parameters to detect and classify the pathogen; and
   a display module to display a result based on the comparison.

2. The device as claimed in claim 1, wherein the image processing module is to compare each of the plurality of spectral parameters with the set of standard spectral parameters based on a first image processing model and wherein the library database is to receive a new set of standard spectral parameters identifiable with a new reference pathogen, wherein the device comprises:
   a model builder ensemble to provide a plurality of image processing models based on the new set of standard spectral parameters identifiable with the new reference pathogen and the set of standard spectral parameters identifiable with reference pathogen; and
   a cross-validator to fix a second image processing model from the plurality of image processing models, wherein the second image processing model is to replace the first image processing model.

3. The device as claimed in claim 1, wherein the plurality of light sources comprises at least one of the following: a light emitting diode, a laser, a colored light source, a configurable light source, ambient light, or any combination thereof.

4. The device as claimed in claim 1, wherein the detector is to capture at least one of a steady state fluorescence spectrum, fluorescence lifetime spectrum, photobleaching spectrum, time-resolved reflectance spectrum, time-resolved transmittance spectrum, and a combination thereof.

5. The device as claimed in claim 4, wherein the detector is to capture fluorescence life time spectra, wherein the excitation radiation has the predetermined duration in the range from about 1 ps to about 1 s and the predetermined periodicity in the range from about 0.01 ns to about 1 s.

6. The device as claimed in claim 4, wherein the detector is to capture photobleaching spectra, wherein the excitation radiation has the predetermined duration in the range from about 1 ms to about 10 s and the predetermined periodicity in the range from about 0.01 s to about 1 min.

7. The device as claimed in claim 1, wherein the image processing module is to classify the pathogen based on family, genus, species and strain based on the comparison.

8. The device as claimed in claim 1, wherein the image processing module is to quantify pathogens present in the sample, wherein the image processing module is to receive an intensity of the time-dependent fluorescence of the sample and compare the intensity with a fluorescence intensity data provided in the library database to quantify pathogens.

9. The device as claimed in claim 1, wherein based on the detection and classification of pathogens, the device is to monitor wound healing and wound closure, wherein the device is to calculate at least one of the following: wound size, wound depth, wound temperature distribution, tissue classification, biofilm information, degree of contamination, tissue oxygenation and blood flow.

10. The device as claimed in claim 1, wherein the plurality of spectral parameters comprises ratios of amplitude of fluorescence emission spectra, ratios of amplitude of reflectance spectra, ratios of amplitude of transmittance spectra, bandwidth of the fluorescence emission spectra, full width half maxima of the fluorescence emission spectra, and combinations thereof.

11. The device as claimed in claim 1, wherein the library database comprises at least one of excitation emission matrix spectra, excitation emission matrix fluorescence spectra, reflectance spectra, transmittance spectra, fluorescence life times, photobleaching times, absorption coefficients, reflection coefficients, transmission coefficients, scattering coefficients, normalized intensity data, intensity ratios, or any combinations thereof, identifiable with various reference pathogens.

12. The device as claimed in claim 1, wherein the device is a handheld device.

13. The device as claimed in claim 1, wherein the image processor is to obtain at least one of the following: fluorescence decay times, fluorescence emission signal amplitude, photobleaching times, or any combination thereof.

14. The device as claimed in claim 1, wherein the result comprises at least one of the following: detection of presence of various pathogens on the sample, pathogen spatial distribution data, pathogen growth state data, co-colonization data, biofilm information, biomarker information, pathogen quantification data, a treatment protocol, or any combination thereof.

15. A method for non-invasive, automatic, and in-situ detection and classification of pathogens comprising:
   exposing a sample comprising a plurality of pathogens to an excitation radiation at a predetermined range of wavelengths from a plurality of light sources for a predetermined duration at a predetermined periodicity;
   synchronously capturing, by a detector, a time-resolved fluorescence emission spectra, time-resolved reflectance, and transmittance spectra at multiple spectral bands from the sample;
   performing, by an image processing module, spatial and temporal resolution of the time-resolved fluorescence emission spectra, time-resolved reflectance, and time-resolved transmittance spectra from the sample to obtain a plurality of spectral parameters;

accessing, by an image processor, a library database, wherein the library database comprises a set of standard spectral parameters associated with reference pathogens;

comparing, by the image processing module, each of the plurality of spectral parameters with the set of standard spectral parameters to detect and classify the pathogens; and displaying, by a display module, a result based on the comparing.

16. The method as claimed in claim 15, wherein the method comprises:

computing, by the image processing module, real time spatial distribution data of the pathogens across the wound region;

combining, by the image processing module, the real time spatial distribution data of the pathogens across the wound region with fluorescence intensity data at a plurality of spectral bands of the corresponding pathogens contained in the library database; and quantifying, by the image processing module, amount of each pathogen across the wound region.

17. The method as claimed in claim 15, the method comprising:

receiving, by the library database, a new set of standard spectral parameters identifiable with a new reference pathogen;

providing, by a model builder ensemble, a plurality of image processing models based on the new set of standard spectral parameters identifiable with the new reference pathogen and the set of standard spectral parameters identifiable with reference pathogen; and fixing, by a cross-validator, a second image processing model from the plurality of image processing models, wherein the second image processing model is to replace a first image processing model, wherein the first image processing model is associated with the set of standard spectral parameters and the second image processing model is associated with the set of standard spectral parameters and the new set of standard spectral parameters.

* * * * *